US012577207B2

(12) United States Patent
Amato et al.

(10) Patent No.: US 12,577,207 B2

(45) Date of Patent: Mar. 17, 2026

(54) INDAZOLE DERIVATIVES AS CANNABINOID RECEPTOR PARTIAL AGONISTS

(71) Applicant: RESEARCH TRIANGLE INSTITUTE, Research Triangle Park, NC (US)

(72) Inventors: George Amato, Cary, NC (US); Rangan Maitra, Cary, NC (US); Scott P. Runyon, Hillsborough, NC (US)

(73) Assignee: RESEARCH TRIANGLE INSTITUTE

( * ) Notice: Subject to any disclaimer, the term of this patent is extended or adjusted under 35 U.S.C. 154(b) by 793 days.

(21) Appl. No.: 17/796,419

(22) PCT Filed: Jan. 29, 2021

(86) PCT No.: PCT/US2021/015815

§ 371 (c)(1),
(2) Date: Jul. 29, 2022

(87) PCT Pub. No.: WO2021/155227

PCT Pub. Date: Aug. 5, 2021

(65) Prior Publication Data

US 2023/0339863 A1 Oct. 26, 2023

Related U.S. Application Data

(60) Provisional application No. 62/967,713, filed on Jan. 30, 2020.

(51) Int. Cl.
*C07D 231/56* (2006.01)

(52) U.S. Cl.
CPC .................................. *C07D 231/56* (2013.01)

(58) Field of Classification Search
CPC .................................................... C07D 231/56
See application file for complete search history.

(56) References Cited

U.S. PATENT DOCUMENTS

2010/0249123 A1* 9/2010 Bonnet ................. C07C 235/56 558/392
2016/0122290 A1 5/2016 Rusche et al.

FOREIGN PATENT DOCUMENTS

WO 2008117175 A2 10/2008
WO 2009/106980 * 9/2009
WO 2009106980 A2 9/2009
WO 2009106982 A1 9/2009
WO 2014/167530 * 10/2014
WO 2014167530 A1 10/2014

OTHER PUBLICATIONS

Daris, Bosn J Basic Med Sci, 2019, vol. 19(1), 14-23. (Year: 2019).*
Bruni, Molecules 2018, 2478, vol. 2, 1-25. (Year: 2018).*
Sarfaraz, Cancer Res 2008, 68(2), 339-342. (Year: 2008).*
Ghasemi, Trends in Endocrinology & Metabolism, 2022, vol. 3(12), 828-849. (Year: 2022).*
Registry(STN)[online], May 29, 2011[date of retrieval: Nov. 26, 2024] CAS Registry No. 1302379-80-1 etc., total 5 compounds.
International Search Report and Written Opinion dated May 12, 2021, prepared in International Application No. PCT/US2021/015815.
Mackie, K. Cannabinoid receptors as therapeutic targets, Annu. Rev. Pharmacol. Toxicol., 46, 101-122.
Howlett, A. C. (2006); Breivogel, C. S.; S.R., C.; Deadwyler, S. A.; Hampson, R. E.; Porrino, L. J. Cannabinoid physiology and pharmacology: 30 years of progress, Neuropharmacology, 47 Suppl 1, 345-358 (2004).
Pertwee, R. G. The therapeutic potential of drugs that target cannabinoid receptors or modulate the tissue levels or actions of endocannabinoids. AAPS Journal, 7, E625-54 (2005).
Christopoulos, A. Allosteric binding sites on cell-surface receptors: novel targets for drug discovery. Nat Rev Drug Discov, 1, 198-210 (2002).
Bridges, T. M.; Lindsley, C. W. G-protein-coupled receptors: from classical modes of modulation to allosteric mechanisms. ACS Chem. Biol., 3, 530-541 (2008).
Adam et al., Low Brain Penetrant CB1 Receptor Agonists for the Treatment of Neuropathic Pain, Bioorganic & Medicinal Chemistry Letters, 22, 2932-2937 (2012).
Cumella et al., Chromenopyrazoles: Non-psychoactive and Selective CB1 Cannabanoid Agonists with Peripheral Antinociceptive Properties, ChemMedChem, 7, 452-463 (2012).
Seltzman, et al., Peripherally Selective Cannabinoid 1 Receptor (CB1R) Agonists for the Treatment of Neuropathic Pain, J Med Chem. Aug. 25, 2016;59(16):7525-43.
Zhang et al., Synthesis and biological evaluation of bivalent ligands for the cannabinoid 1 receptor, J Med Chem. Oct. 14, 2010;53(19):7048-60.
Dimarzo, V. et al., "Endocannabinoids: new targets for drug development", Curr Pharm Des, 6, 1361-80 (2000).

* cited by examiner

*Primary Examiner* — D Margaret M Seaman
(74) *Attorney, Agent, or Firm* — Barnes & Thornburg LLP

(57) ABSTRACT

The present disclosure includes peripheral partial agonists of one or more CB receptors, including modulation of CB1, both with and without CB2 selectivity. The compounds of the present disclosure may be useful in the treatment of diseases and disorders mediated by a CB-signaling pathway, including but not limited to pain, gastrointestinal disorders, metabolic disorders, and liver disorders, such as alcoholic steatohepatitis or nonalcoholic steatohepatitis (NASH).

10 Claims, No Drawings

INDAZOLE DERIVATIVES AS CANNABINOID RECEPTOR PARTIAL AGONISTS

CROSS-REFERENCE TO RELATED APPLICATION

The present application claims the benefit of and priority to U.S. Provisional Application No. 62/967,713, filed Jan. 30, 2020, the contents of which are incorporated herein by reference in their entirety.

This application is a National Stage application of International Application No. PCT/US2021/015815, filed Jan. 29, 2021, which claims the benefit of U.S. Provisional Application No. 62/967,713, filed Jan. 30, 2020.

FEDERALLY SPONSORED RESEARCH

This invention was made with government support under R01 DK100414 and R01 AA022235 which both were awarded by National Institutes of Health. The government has certain rights in the invention.

FIELD OF THE INVENTION

The present invention provides novel cannabinoid (CB) receptor partial agonists and uses therefor. The compounds of the present invention are believed to be useful for the treatment of diseases and conditions caused by physiological processes implicating the cannabinoid receptor, including appetite control, cardiovascular regulation, metabolic syndromes, liver diseases, pain regulation, learning and memory, gastrointestinal disorders, inflammatory disorders, and drug dependence.

BACKGROUND OF THE INVENTION

The cannabinoid CB1 and CB2 receptors are components of the endocannabinoid system which is involved in many important physiological processes such as cardiovascular regulation, learning and memory, appetite, and pain control. See, for example, Mackie, K. Cannabinoid receptors as therapeutic targets, *Annu. Rev. Pharmacol. Toxicol.,* 46, 101-122; Howlett, A. C. (2006); Breivogel, C. S.; S. R., C.; Deadwyler, S. A.; Hampson, R. E.; Porrino, L. J. Cannabinoid physiology and pharmacology: 30 years of progress, *Neuropharmacology,* 47 Suppl 1, 345-358 (2004); and Di, M.; Bisogno, T.; De Petrocellis, L. Endocannabinoids: new targets for drug development, *Curr Pharm Des,* 6, 1361-80 (2000); each herein incorporated by reference with regarding to such background teaching.

CB receptors have been demonstrated as a viable targets in a number of disorders including obesity, drug addiction, pain, inflammation, gastrointestinal diseases, liver diseases, multiple sclerosis, psychosis, schizophrenia, and osteoporosis. See, Pertwee, R. G. The therapeutic potential of drugs that target cannabinoid receptors or modulate the tissue levels or actions of endocannabinoids. *AAPS Journal,* 7, E625-54 (2005); herein incorporated by reference with regard to such teaching. A wide range of selective and non-selective agonists and antagonists for CB1 and CB2 receptors have been developed thus far. Currently, licensed cannabinoid medications all contain tetrahydrocannabinol ($\Delta^9$-THC), the principal psychoactive constituent of the plant *cannabis* or its synthetic analog (nabilone); however, they are prescribed with many restrictions because of their adverse effects such as marijuana-like psychoactivity and addictive tendency. The CB1 selective antagonist/inverse agonist Rimonabant (SR141716A) was first approved for treatment of obesity but was subsequently withdrawn due to a risk of suicidal ideation. The limited therapeutic window due to psychoactive effects restricts the potential for CB-mediated therapeutics.

One alternate approach to target the CB1-mediated signaling pathways is to develop allosteric modulators that bind to distinct binding sites from the orthosteric site. See, for example, Christopoulos, A. Allosteric binding sites on cell-surface receptors: novel targets for drug discovery. *Nat Rev Drug Discov,* 1, 198-210 (2002); and Bridges, T. M.; Lindsley, C. W. G-protein-coupled receptors: from classical modes of modulation to allosteric mechanisms. *ACS Chem. Biol.,* 3, 530-541 (2008); each incorporated herein with regard to such background teaching. Another alternate approach to target the CB1-mediated signaling pathways is to develop peripherally restricted full agonists. See, for example, Adam et al., Low Brain Penetrant CB1 Receptor Agonists for the Treatment of Neuropathic Pain, *Bioorganic & Medicinal Chemistry Letters,* 22, 2932-2937 (2012); and Cumella et al., Chromenopyrazoles: Non-psychoactive and Selective CB1 Cannabanoid Agonists with Peripheral Antinociceptive Properties, *ChemMedChem,* 7, 452-463 (2012), each incorporated by reference with regard to such background teaching of peripherally restricted full agonists.

There is a need for developing additional alternative approaches to achieve the beneficial effects of CB-mediated therapeutics without the negative side effects associated with CNS penetrating modulators.

BRIEF SUMMARY OF THE INVENTION

The present disclosure includes peripheral partial agonists of the CB receptors, including CB1 both with and without CB2 selectivity. The compounds of the present disclosure may be useful in the treatment of diseases and disorders mediated by a CB-signaling pathway, including but not limited to pain, gastrointestinal disorders, and metabolic disorders including liver disorders, such as both nonalcoholic steatohepatitis (NASH) and alcoholic steatohepatitis (ASH).

One embodiment of the present disclosure includes a compound of Formula (I):

(I)

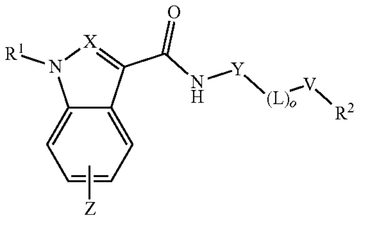

wherein $R^1$ is unsubstituted or substituted $C_{1-10}$ alkyl, $C_{1-10}$ haloalkyl, $(CH_2)_n$-cycloalkyl, $(CH_2)_n$-heterocyclyl, $(CH_2)_n$-aryl, or $(CH_2)_n$-heteroaryl;

n is 1, 2, or 3;

X is CH or N;

Y is $CHR^3$ or $CR^4R^5$;

$R^3$ is $C_{1-4}$ alkyl;

each of $R^4$ and $R^5$ independently is a $C_{1-4}$ alkyl; or $R^4$ and $R^5$ may combine with the carbon atom to which they are attached to form a 3- to 7-membered cycloalkyl or heterocycloalkyl ring;

L is divalent $C_{1-3}$ alkyl or $C_{2-3}$ alkenyl;

o is 0 or 1;

V is divalent aryl, heteroaryl, cycloalkyl, heterocyclyl, $C_{2-3}$ alkyl, or $C_{2-3}$ alkenyl;

Z is H, F, Cl, $CF_3$, Me, CN, OMe, $OCF_3$, or $OCHF_2$;

$R^2$ is (i) $(CH_2)_pC(O)NHR^a$;

(ii) $NHC(O)R^b$;

(iii) $NR^cC(O)NHR^a$; or (iv) $NH(C{=}NR^d)NHR^a$;

p is 0, 1, or 2;

$R^a$ is H, $C_{1-4}$ alkyl, $C_{3-6}$ cycloalkyl, heterocyclyl, aryl, or heteroaryl;

$R^b$ is $C_{1-4}$ alkyl, $C_{3-6}$ cycloalkyl, heterocyclyl, aryl, or heteroaryl;

$R^c$ is H or $C_{1-4}$ alkyl; and $R^d$ is H, CN, $C_{1-4}$ alkyl, or $C_{3-6}$ cycloalkyl, or a pharmaceutically acceptable salt thereof.

One aspect includes wherein X is N. One aspect includes wherein Y is $CR^4R^5$. One aspect includes wherein Y is $C(CH_3)_2$. One aspect includes wherein V is divalent aryl, heteroaryl, cycloalkyl, or heterocyclyl. One aspect includes wherein $R^2$ is $(CH_2)_pC(O)NHR^a$; $NHC(O)R^b$; or $NHC(O)NHR^a$, and wherein $R^a$ is H, $C_{1-4}$ alkyl, $C_{3-6}$ cycloalkyl, heterocyclyl, aryl, or heteroaryl; and $R^b$ is $C_{1-4}$ alkyl, $C_{3-6}$ cycloalkyl, heterocyclyl, aryl, or heteroaryl. One aspect includes wherein $R^2$ is $(CH_2)_pC(O)NHR^a$; or $NHC(O)NHR^a$, wherein $R^a$ is H, $C_{1-4}$ alkyl, $C_{3-6}$ cycloalkyl, heterocyclyl, aryl, or heteroaryl. One aspect includes wherein o is 0. One aspect includes wherein o is 1 and L is divalent $C_{1-3}$ alkyl. One aspect includes wherein n is 1. One aspect includes wherein Z is H or F.

One embodiment of the present disclosure includes a method for the treatment of a disease in a mammal susceptible to modulation of one or more CB receptors which comprises administration of an effective amount of a compound of the present disclosure. In one aspect, the disease is inhibition of angiogenesis, inhibition of tumor growth, cancer, endometrial cancer, hepatocellular carcinoma, ovarian cancer, breast cancer, pancreatic cancer, colorectal cancer, lung cancer, prostate cancer, desmotrophic small round cell tumors, renal cell carcinoma, pain, chronic pain, acute pain, somatic pain, visceral pain, neuropathic pain, inflammatory pain, infertility, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, a metabolic disorder, obesity, a liver disorder, a liver disease, steatosis, steatohepatitis, alcoholic steatohepatitis, or nonalcoholic steatohepatitis (NASH). In one aspect, the disease is a metabolic disorder, obesity, a liver disorder, a liver disease, steatosis, steatohepatitis, alcoholic steatohepatitis, or nonalcoholic steatohepatitis (NASH). In one aspect, the disease is a metabolic disorder and is diabetes, type 2 diabetes, Gaucher's disease, glucose galactose malabsorption, hemochromatosis, phenylketonuria, Niemann-Pick disease, Fabry's disease, medium-chain acyl-coenzyme A dehydrogenase deficiency, metabolic syndrome, or obesity. In one aspect, the disease is a liver disorder or a liver disease and is fatty liver disease, alcoholic fatty liver disease (AFLD), alcoholic steatohepatitis (ASH), nonalcoholic fatty liver disease (NAFLD), nonalcoholic steatohepatitis (NASH), liver fibrosis, cirrhosis, autoimmune hepatitis, primary biliary cirrhosis, or primary sclerosing cholangitis.

One embodiment of the present disclosure includes a pharmaceutical composition comprising a compound of the present disclosure and one or more pharmaceutically acceptable carrier.

One embodiment of the present disclosure includes use of a compound of the present disclosure for the preparation of a medicament for the treatment of a disease in a mammal susceptible to modulation of one or more CB receptors, which comprises administration of an effective amount of the compound. In one aspect, the disease is inhibition of angiogenesis, inhibition of tumor growth, cancer, endometrial cancer, hepatocellular carcinoma, ovarian cancer, breast cancer, pancreatic cancer, colorectal cancer, lung cancer, prostate cancer, desmotrophic small round cell tumors, renal cell carcinoma, pain, chronic pain, acute pain, somatic pain, visceral pain, neuropathic pain, inflammatory pain, infertility, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, a metabolic disorder, obesity, a liver disorder, a liver disease, steatosis, steatohepatitis, alcoholic steatohepatitis, or nonalcoholic steatohepatitis (NASH). In one aspect, the disease is a metabolic disorder, obesity, a liver disorder, a liver disease, steatosis, steatohepatitis, alcoholic steatohepatitis, or nonalcoholic steatohepatitis (NASH). In one aspect, the disease is a metabolic disorder and is diabetes, type 2 diabetes, Gaucher's disease, glucose galactose malabsorption, hemochromatosis, phenylketonuria, Niemann-Pick disease, Fabry's disease, medium-chain acyl-coenzyme A dehydrogenase deficiency, metabolic syndrome, or obesity. In one aspect, the disease is a liver disorder or a liver disease and is fatty liver disease, alcoholic fatty liver disease (AFLD), alcoholic steatohepatitis (ASH), nonalcoholic fatty liver disease (NAFLD), nonalcoholic steatohepatitis (NASH), liver fibrosis, cirrhosis, autoimmune hepatitis, primary biliary cirrhosis, or primary sclerosing cholangitis.

One embodiment of the present disclosure includes a compound of the present disclosure for use as an active therapeutic substance. One embodiment includes a compound of the present disclosure for use in the treatment of a disease mediated by one or more CB receptors. In one aspect, the disease is inhibition of angiogenesis, inhibition of tumor growth, cancer, endometrial cancer, hepatocellular carcinoma, ovarian cancer, breast cancer, pancreatic cancer, colorectal cancer, lung cancer, prostate cancer, desmotrophic small round cell tumors, renal cell carcinoma, pain, chronic pain, acute pain, somatic pain, visceral pain, neuropathic pain, inflammatory pain, infertility, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, a metabolic disorder, obesity, a liver disorder, a liver disease, steatosis, steatohepatitis, alcoholic steatohepatitis, or nonalcoholic steatohepatitis (NASH). In one aspect, the disease is a metabolic disorder, obesity, a liver disorder, a liver disease, steatosis, steatohepatitis, alcoholic steatohepatitis, or nonalcoholic steatohepatitis (NASH). In one aspect, the disease is a metabolic disorder and is diabetes, type 2 diabetes, Gaucher's disease, glucose galactose malabsorption, hemochromatosis, phenylketonuria, Niemann-Pick disease, Fabry's disease, medium-chain acyl-coenzyme A dehydrogenase deficiency, metabolic syndrome, or obesity. In one aspect, the disease is a liver disorder or a liver disease and is fatty liver disease, alcoholic fatty liver disease (AFLD), alcoholic steatohepatitis (ASH), nonalcoholic fatty liver disease (NAFLD), nonalcoholic steatohepatitis (NASH), liver fibrosis, cirrhosis, autoimmune hepatitis, primary biliary cirrhosis, or primary sclerosing cholangitis.

One embodiment of the present disclosure includes a method for treating one or more disease selected from inhibition of angiogenesis, inhibition of tumor growth, cancer, endometrial cancer, hepatocellular carcinoma, ovarian cancer, breast cancer, pancreatic cancer, colorectal cancer, lung cancer, prostate cancer, desmotrophic small round cell tumors, renal cell carcinoma, pain, chronic pain, acute pain, somatic pain, visceral pain, neuropathic pain, inflammatory pain, infertility, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, a metabolic disorder, obesity, a liver disorder, a liver disease, steatosis, steatohepatitis, alcoholic steatohepatitis, or nonalcoholic steatohepatitis (NASH) comprising administering an effective amount of a compound of the present disclosure. In one aspect, the disease is a metabolic disorder, obesity, a liver disorder, a liver disease, steatosis, steatohepatitis, alcoholic steatohepatitis, or nonalcoholic steatohepatitis (NASH). In one aspect, the disease is a metabolic disorder and is diabetes, type 2 diabetes, Gaucher's disease, glucose galactose malabsorption, hemochromatosis, phenylketonuria, Niemann-Pick disease, Fabry's disease, medium-chain acyl-coenzyme A dehydrogenase deficiency, metabolic syndrome, or obesity. In one aspect, the disease is a liver disorder or a liver disease and is fatty liver disease, alcoholic fatty liver disease (AFLD), alcoholic steatohepatitis (ASH), nonalcoholic fatty liver disease (NAFLD), nonalcoholic steatohepatitis (NASH), liver fibrosis, cirrhosis, autoimmune hepatitis, primary biliary cirrhosis, or primary sclerosing cholangitis.

One embodiment of the present disclosure includes use of a compound of the present disclosure for the preparation of a medicament for the treatment of one or more disease selected from inhibition of angiogenesis, inhibition of tumor growth, cancer, endometrial cancer, hepatocellular carcinoma, ovarian cancer, breast cancer, pancreatic cancer, colorectal cancer, lung cancer, prostate cancer, desmotrophic small round cell tumors, renal cell carcinoma, pain, chronic pain, acute pain, somatic pain, visceral pain, neuropathic pain, inflammatory pain, infertility, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, a metabolic disorder, obesity, a liver disorder, a liver disease, steatosis, steatohepatitis, alcoholic steatohepatitis, or nonalcoholic steatohepatitis (NASH), which comprises administration of an effective amount of the compound. In one aspect, the disease is a metabolic disorder, obesity, a liver disorder, a liver disease, steatosis, steatohepatitis, alcoholic steatohepatitis, or nonalcoholic steatohepatitis (NASH). In one aspect, the disease is a metabolic disorder and is diabetes, type 2 diabetes, Gaucher's disease, glucose galactose malabsorption, hemochromatosis, phenylketonuria, Niemann-Pick disease, Fabry's disease, medium-chain acyl-coenzyme A dehydrogenase deficiency, metabolic syndrome, or obesity. In one aspect, the disease is a liver disorder or a liver disease and is fatty liver disease, alcoholic fatty liver disease (AFLD), alcoholic steatohepatitis (ASH), nonalcoholic fatty liver disease (NAFLD), nonalcoholic steatohepatitis (NASH), liver fibrosis, cirrhosis, autoimmune hepatitis, primary biliary cirrhosis, or primary sclerosing cholangitis.

One embodiment of the present disclosure includes a compound of the present disclosure for use in the treatment of one or more disease selected from inhibition of angiogenesis, inhibition of tumor growth, cancer, endometrial cancer, hepatocellular carcinoma, ovarian cancer, breast cancer, pancreatic cancer, colorectal cancer, lung cancer, prostate cancer, desmotrophic small round cell tumors, renal cell carcinoma, pain, chronic pain, acute pain, somatic pain, visceral pain, neuropathic pain, inflammatory pain, infertility, atherosclerosis, hypertension, hemorrhagic shock, cardiogenic shock, hypercholesterolemia, dyslipidemia, diabetes, retinopathy, glaucoma, anxiety, gastrointestinal disorders, intestinal hypomotility, a metabolic disorder, obesity, a liver disorder, a liver disease, steatosis, steatohepatitis, alcoholic steatohepatitis, or nonalcoholic steatohepatitis (NASH). In one aspect, the disease is a metabolic disorder, obesity, a liver disorder, a liver disease, steatosis, steatohepatitis, alcoholic steatohepatitis, or nonalcoholic steatohepatitis (NASH). In one aspect, the disease is a metabolic disorder and is diabetes, type 2 diabetes, Gaucher's disease, glucose galactose malabsorption, hemochromatosis, phenylketonuria, Niemann-Pick disease, Fabry's disease, medium-chain acyl-coenzyme A dehydrogenase deficiency, metabolic syndrome, or obesity. In one aspect, the disease is a liver disorder or a liver disease and is fatty liver disease, alcoholic fatty liver disease (AFLD), alcoholic steatohepatitis (ASH), nonalcoholic fatty liver disease (NAFLD), nonalcoholic steatohepatitis (NASH), liver fibrosis, cirrhosis, autoimmune hepatitis, primary biliary cirrhosis, or primary sclerosing cholangitis.

Preferably, the compounds of the present disclosure may be used where CB receptor agents may exhibit greater potency and experience reduced side effects, resulting in improved efficacy, pharmacokinetics, and safety.

The compounds of the present disclosure are believed useful as peripheral partial agonists of one or more CB receptors, including modulation of CB1, both with and without CB2 selectivity. The compounds of the present disclosure may be useful in the treatment of diseases and disorders mediated by a CB-signaling pathway, including but not limited to pain, gastrointestinal disorders, and metabolic disorders including liver disorders, such as nonalcoholic steatohepatitis (NASH).

The scope of the present invention includes all combinations of aspects, embodiments, and preferences herein described.

DETAILED DESCRIPTION OF THE INVENTION

The following definitions are meant to clarify, but not limit, the terms defined. If a particular term used herein is not specifically defined, such term should not be considered indefinite. Rather, terms are used within their accepted meanings.

As used throughout this specification, the preferred number of atoms, such as carbon atoms, will be represented by, for example, the phrase "$C_{x-y}$ alkyl," which refers to an alkyl group, as herein defined, containing the specified number of carbon atoms. Similar terminology will apply for other preferred terms and ranges as well. Thus, for example, $C_{1-4}$ alkyl represents a straight or branched chain hydrocarbon containing one to four carbon atoms.

As used herein the term "alkyl" alone or in combination with any other term, refers to a straight or branched chain hydrocarbon. Examples of "alkyl" as used herein include, but are not limited to, methyl, ethyl, propyl, isopropyl, isobutyl, n-butyl, tert-butyl, sec-butyl, iso-pentyl, n-pentyl, n-hexyl, and the like. The alkyl group may be substituted or unsubstituted.

As used herein the term "alkenyl" refers to a straight or branched chain aliphatic hydrocarbon containing one or more carbon-to-carbon double bonds, which may be optionally substituted, with multiple degrees of substitution being allowed. Examples of "alkenyl" as used herein include, but are not limited to, vinyl, and allyl.

As used herein, the term "alkylene" refers to an optionally substituted straight divalent hydrocarbon radical. Examples of "alkylene" as used herein include, but are not limited to, methylene, ethylene, n-propylene, n-butylene, and the like.

As used herein the term "alkynyl" refers to a straight or branched chain aliphatic hydrocarbon containing one or more carbon-to-carbon triple bonds, which may be optionally substituted, with multiple degrees of substitution being allowed. An example of "alkynyl" as used herein includes, but is not limited to, ethynyl.

As used herein, the term "cycloalkyl" refers to a fully saturated optionally substituted monocyclic, bicyclic, or bridged hydrocarbon ring, with multiple degrees of substitution being allowed. Exemplary "cycloalkyl" groups as used herein include, but are not limited to, cyclopropyl, cyclobutyl, cyclopentyl, cyclohexyl, and cycloheptyl.

As used herein The term "heterocycle," or "heterocyclic" as used herein, means a cycloalkyl group wherein one or more of the carbon atoms replaced by N, O, S, or Si. The heterocycle may be connected to the parent molecular moiety through any carbon atom or any nitrogen atom contained within the heterocycle. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. Representative examples of bicyclic heterocycle include, but are not limited to 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl and 1,2,3,4-tetrahydroquinolinyl. The term heterocycle also include bridged heterocyclic systems such as azabicyclo[3.2.1]octane, azabicyclo[3.3.1]nonane and the like. The heterocycle and be substituted or unsubstituted.

As used herein, the term "heterocyclyl" refers to a non-aromatic monocyclic ring or fused non-aromatic polycyclic rings with one or more heteroatom(s) independently selected from N, S and O, with the remaining ring atoms being carbon and wherein at least one heteroatom is present in each non-aromatic ring. The heterocyclyl group may be a three-member ring, a four member ring, a five member ring, a six member ring or a seven member ring. In certain embodiments, the heterocyclyl group is 1,4-dioxane, 1,3-dioxolane, 1,4-dithiane, imidazolidine, morpholine, piperidine, piperidone, piperazine, pyrolidone, pyrrolidine, or 1,3,5-trithiane. It may contain an imide. The heterocyclyl group may be bicyclic such as an heterospiro group, e.g., heterospiro[3.3] heptanyl, heterospiro[3.4] octanyl, or heterospiro[5.5] undecanyls. The heterocyclyl group may be substituted or unsubstituted. Thus, heterocyclyl group encompasses heterocycloalkyl groups substituted with one or more halogens, such as 3,3-difluoropiperidine, or 4,4-difluoropiperidine. In addition, the heterocyclyl group may be substituted with a $C_1$-$C_4$ alkyl or $C_1$-$C_4$ halo alkyl group such as a —$CF_3$ group.

As used herein, the term "aryl" refers to a single benzene ring or fused benzene ring system which may be optionally substituted, with multiple degrees of substitution being allowed. Examples of "aryl" groups as used include, but are not limited to, phenyl, 2-naphthyl, 1-naphthyl, anthracene, and phenanthrene. Preferable aryl rings have six- to ten-members.

As used herein, a fused benzene ring system encompassed within the term "aryl" includes fused polycyclic hydrocarbons, namely where a cyclic hydrocarbon with less than maximum number of noncumulative double bonds, for example where a saturated hydrocarbon ring (cycloalkyl, such as a cyclopentyl ring) is fused with an aromatic ring (aryl, such as a benzene ring) to form, for example, groups such as indanyl and acenaphthylenyl, and also includes such groups as, for non-limiting examples, dihydronaphthalene and tetrahydronaphthalene.

As used herein, the term "heteroaryl" refers to a monocyclic five to seven membered aromatic ring, or to a fused bicyclic aromatic ring system comprising two of such aromatic rings, which may be optionally substituted, with multiple degrees of substitution being allowed. Preferably, such rings contain five- to ten-members. These heteroaryl rings contain one or more nitrogen, sulfur, and/or oxygen atoms, where N-oxides, sulfur oxides, and dioxides are permissible heteroatom substitutions. Examples of "heteroaryl" groups as used herein include, but are not limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzoxazole, benzothiophene, indole, indazole, benzimidazole, imidazopyridine, pyrazolopyridine, and pyrazolopyrimidine.

As used herein the term "halogen" refers to fluorine, chlorine, bromine, or iodine.

As used herein the term "haloalkyl" refers to an alkyl group, as defined herein, which is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —$CF_3$.

As used herein, the term "substituted" refers to a group in which one or more hydrogen atoms are each independently replaced with the same or different substituent(s). Typical substituents include, but are not limited to, CN, $NO_2$, OH, oxo, $C_1$-$C_6$ alkoxy, $OC_1$-$C_6$ haloalkyl, $SC_1$-$C_6$ alkyl, $SC_1$-$C_6$ haloalkyl, halogen, $C_1$-$C_6$ alkyl, $C_1$-$C_6$ haloalkyl, $CO_2H$, $NH_2$, $NH(C_1$-$C_3$ alkyl), $N(C_{1-3}$ alkyl$)_2$, $SO_2H$, $NHSO_2C_1$-$C_3$ alkyl, $SO_2NH_2$, $SO_2C_1$-$C_3$ alkyl, $NHC(OXC_1$-$C_3$ alkyl), and $C_3$-$C_6$ cycloalkyl.

Typically, but not absolutely, the salts of the present invention are pharmaceutically acceptable salts. Salts encompassed within the term "pharmaceutically acceptable salts" refer to non-toxic salts of the compounds of this invention. Salts of the compound of the present invention may comprise acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

The compounds of formula (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

As used herein, the term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I), as well as salts or solvates thereof, may be administered as the raw chemical. Additionally, the active ingredient may be presented as a pharmaceutical composition.

Accordingly, the invention further provides pharmaceutical compositions that include effective amounts of one or more compounds of the formula (I), or a salt or solvate thereof, and one or more pharmaceutically acceptable carriers, diluents, or excipients. The compound of formula (I) or a salt or solvate thereof, are as herein described. The carrier(s), diluent(s), or excipient(s) must be acceptable, in the sense of being compatible with the other ingredients of the formulation and not deleterious to the recipient of the pharmaceutical composition.

The compounds of this invention may be made by a variety of methods, including well-known standard synthetic methods. Illustrative general synthetic methods are set out below and then specific compounds of the invention are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1999) *Protecting Groups in Organic Synthesis, 3rd Edition*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention.

The present invention also provides a method for the synthesis of compounds of formula (I) and novel compounds useful as synthetic intermediates in the preparation of compounds of the present invention.

The compounds can be prepared according to the methods described below using readily available starting materials and reagents. In these reactions, variants may be employed which are themselves known to those of ordinary skill in this art but are not mentioned in greater detail.

Unless otherwise stated, structures depicted herein are also meant to include compounds which differ only in the presence of one or more isotopically enriched atoms. Compounds having the present structure except for the replacement of a hydrogen atom by a deuterium or tritium, or the replacement of a carbon atom by a $^{13}C$- or $^{14}C$-enriched carbon are within the scope of the invention. For example, deuterium has been widely used to examine the pharmacokinetics and metabolism of biologically active compounds. Although deuterium behaves similarly to hydrogen from a chemical perspective, there are significant differences in bond energies and bond lengths between a deuterium-carbon bond and a hydrogen-carbon bond. Consequently, replacement of hydrogen by deuterium in a biologically active compound may result in a compound that generally retains its biochemical potency and selectivity but manifests significantly different absorption, distribution, metabolism, and/or excretion (ADME) properties compared to its isotope-free counterpart. Thus, deuterium substitution may result in improved drug efficacy, safety, and/or tolerability for some biologically active compounds.

In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

The therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of formula (I) for the treatment of humans suffering from frailty, generally, should be in the range of 0.1 to 100 mg/kg body weight of recipient (mammal) per day. More usually the effective amount should be in the range of 0.1 to 20 mg/kg body weight per day. Thus, for a 70 kg adult mammal one example of an actual amount per day would usually be from 10 to 2000 mg. This amount may be given in a single dose per day or in a number (such as two, three, four, five, or more) of sub-doses per day such that the total daily dose is the same. An effective amount of a salt or solvate thereof, may be determined as a proportion of the effective amount of the compound of formula (I) per se. Similar dosages should be appropriate for treatment of the other conditions referred to herein. Pharmaceutical formulations may be presented in unit dose forms containing a predetermined amount of active ingredient per unit dose. Such a unit may contain, as a non-limiting example, 1 mg to 2 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the invention, with regard to certain conditions and disorders for which the compounds of the present invention are believed useful certain routes will be preferable to others. In addition, pharmaceutical formulations may be used to allow delayed or extended exposure to compound of formula (I) under circumstances where delayed or extended exposure would improve therapy.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, alginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

Pharmaceutical formulations adapted for topical administration in the mouth include lozenges, pastilles, and mouthwashes.

A compound of the present invention or a salt or solvate thereof, may be employed alone or in combination with other therapeutic agents. The compound of formula (I) and the other pharmaceutically active agent(s) may be administered together or separately and, when administered separately, administration may occur simultaneously or sequentially, in any order. The amounts of the compound of formula (I) and the other pharmaceutically active agent(s) and the relative timings of administration will be selected in order to achieve the desired combined therapeutic effect. The administration in combination of a compound of formula (I) or a salt or solvate thereof with other treatment agents may be in combination by administration concomitantly in: (1) a unitary pharmaceutical composition including a combination of compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

Those skilled in the art of organic synthesis will appreciate that there exist multiple means of producing compounds of the present invention which are labeled with a radioisotope appropriate to various uses.

Compound Synthesis

One method to prepare the indazoles of the present disclosure includes synthesis of intermediates 3 according to the following Scheme 1. Preparation of 3 began with the commercially available indazole 3-carboxy esters 1, which were N-alkylated and then hydrolyzed, to provide the carboxylic acids 2 (reactions a & b). The carboxylic acids 2 were coupled to an amine to provide the amides 3 (reaction c).

Scheme 1

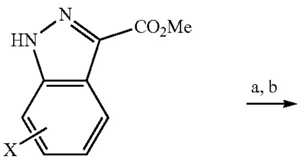

1

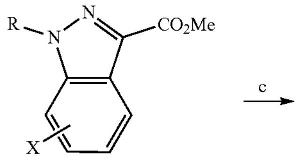

2

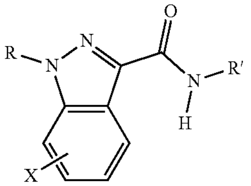

3

In Scheme 1, the reagents and conditions include: (a) RBr, $K_2CO_3$, MeCN, 60° C.; (b) 2 N NaOH, dioxane, 50° C.; and (c) $R'NH_2$, HBTU, $NEt_3$, MeCN, 50° C.

Amides and ureas were then prepared from intermediates 3 using procedures shown in Scheme 2. As shown, aryl carboxamide products were synthesized from aryl bromides such as 4. The aryl bromide was converted to an aryl nitrile using a palladium catalyzed reaction (reaction a, part 1). The aryl nitrile was then hydrolyzed to an aryl carboxamide 5 using aqueous base and hydrogen peroxide (reaction a, part 2).

Alternatively, aryl bromides 4 were directly converted to the carboxamides via lithiation with n-BuLi followed by reaction with trimethylsilyl-isocyanate (TMS-NCO, reaction b).

For piperidine containing products such as 7, Boc protected piperidine intermediates such as 6 were hydrolyzed with aqueous acid (reaction c) and then reacted with TMS-NCO to provide ureas (reaction d, $R''=C(=O)NH_2$) or alkylated with chloroacetamide to provide carboxamides (reaction e, $R''=CH_2C(=O)NH_2$).

Aryl ureas such as 9 were prepared from anilines such as 8. Unsubstituted aryl ureas 9 (R'=H) were prepared by reaction of aniline 8 with TMS-NCO (reaction f). Substituted aryl ureas 9 were prepared by reaction of 8 with a carbamoyl chloride (reaction g).

Scheme 2

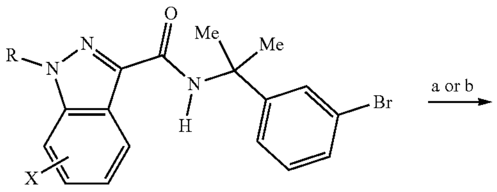

4

-continued

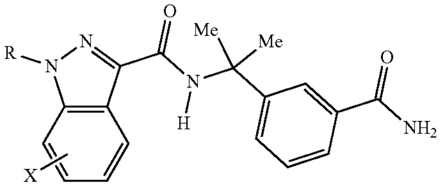

5

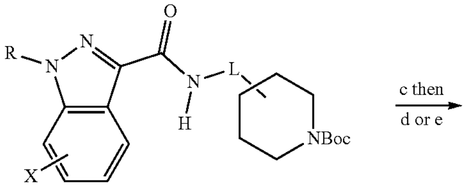

6

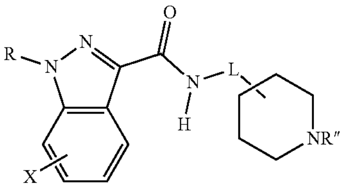

7

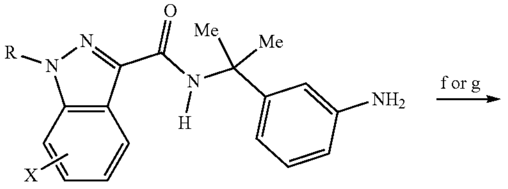

8

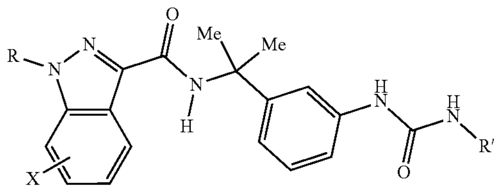

9

In Scheme 2, the reagents and conditions include: (a) (1) $Zn(CN)_2$, $Pd(PPh_3)_4$, DMF, 70° C.; (a) (2) 6 N NaOH, 50% $H_2O_2$, EtOH, rt; $(b)_n$-BuLi, THF, −78° C. then TMS-CN, rt; (c) 6 N HCl, EtOH, 55° C.; (d) TMS-NCO, DCE, rt; (e) $ClCH_2CONH_2$, $K_2CO_3$, MeCN, 50° C.; (f) TMS-NCO, DCE, 60° C.; and (g) R'NHCOCl, Pyridine, DCE, rt.

Indole based products were prepared as for the indazoles, using the same procedures and analogous commercially available starting materials.

TABLE 1
| Synthetic Examples | | |
|---|---|---|
| Example # | Structure | Name |
| 10 | 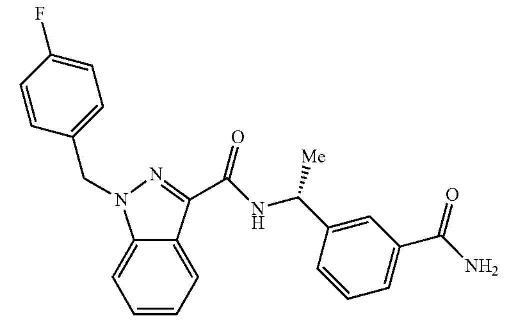 [SMILES: C[C@@H](NC(=O)c1nn(Cc2ccc(F)cc2)c2ccccc12)c1cccc(C(N)=O)c1] | N-[(1R)-1-(3-carbamoylphenyl)ethyl]-1-[(4-fluorophenyl)methyl]-1H-indazole-3-carboxamide |
| 11 | 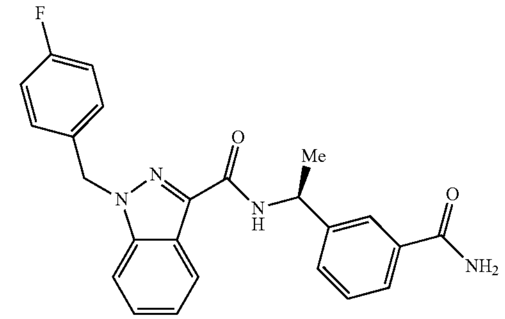 [SMILES: C[C@H](NC(=O)c1nn(Cc2ccc(F)cc2)c2ccccc12)c1cccc(C(N)=O)c1] | N-[(1S)-1-(3-carbamoylphenyl)ethyl]-1-[(4-fluorophenyl)methyl]-1H-indazole-3-carboxamide |
| 12 | 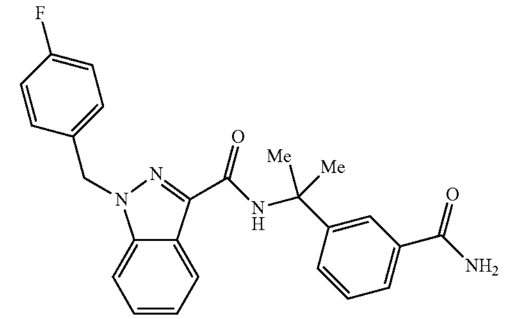 [SMILES: CC(C)(NC(=O)c1nn(Cc2ccc(F)cc2)c2ccccc12)c1cccc(C(N)=O)c1] | N-[2-(3-carbamoylphenyl)propan-2-yl]-1-[(4-fluorophenyl)methyl]-1H-indazole-3-carboxamide |
| 13 | 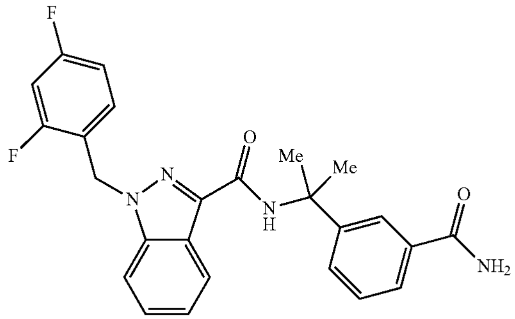 [SMILES: CC(C)(NC(=O)c1nn(Cc2ccc(F)cc2F)c2ccccc12)c1cccc(C(N)=O)c1] | N-[2-(3-carbamoylphenyl)propan-2-yl]-1-[(2,4-difluorophenyl)methyl]-1H-indazole-3-carboxamide |

TABLE 1-continued

| Synthetic Examples | | |
|---|---|---|
| Example # | Structure | Name |
| 14 | 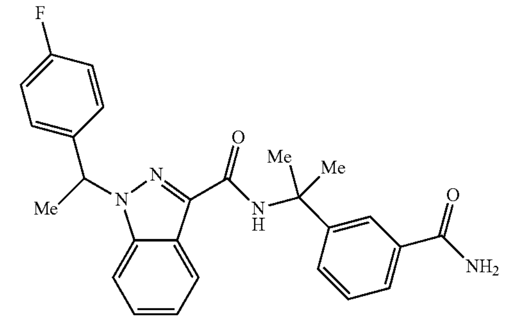 [SMILES: CC(c1ccc(F)cc1)n1nc(C(=O)NC(C)(C)c2cccc(C(N)=O)c2)c2ccccc21] | N-[2-(3-carbamoylphenyl)propan-2-yl]-1-[1-(4-fluorophenyl)ethyl]-1H-indazole-3-carboxamide |
| 15 | 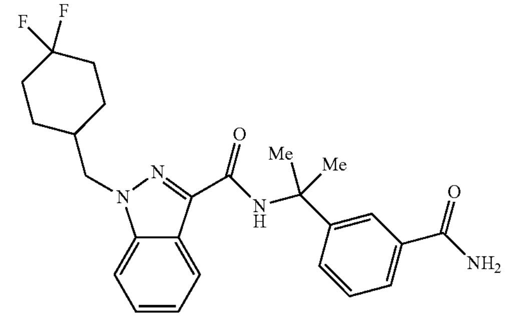 [SMILES: CC(C)(NC(=O)c1nn(CC2CCC(F)(F)CC2)c2ccccc12)c1cccc(C(N)=O)c1] | N-[2-(3-carbamoylphenyl)propan-2-yl]-1-[(4,4-difluorocyclohexyl)methyl]-1H-indazole-3-carboxamide |
| 16 | 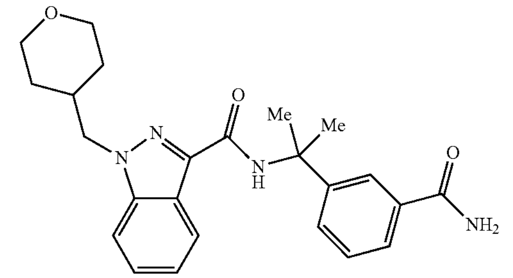 [SMILES: CC(C)(NC(=O)c1nn(CC2CCOCC2)c2ccccc12)c1cccc(C(N)=O)c1] | N-[2-(3-carbamoylphenyl)propan-2-yl]-1-(oxan-4-ylmethyl)-1H-indazole-3-carboxamide |
| 17 | 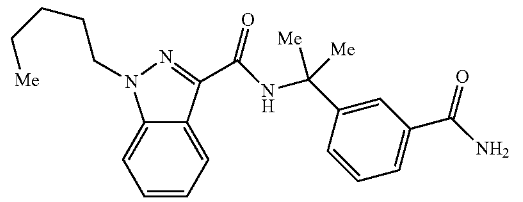 [SMILES: CCCCCn1nc(C(=O)NC(C)(C)c2cccc(C(N)=O)c2)c2ccccc21] | N-[2-(3-carbamoylphenyl)propan-2-yl]-1-pentyl-1H-indazole-3-carboxamide |
| 18 | 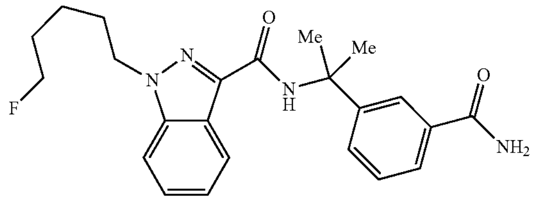 [SMILES: CC(C)(NC(=O)c1nn(CCCCCF)c2ccccc12)c1cccc(C(N)=O)c1] | N-[2-(3-carbamoylphenyl)propan-2-yl]-1-(5-fluoropentyl)-1H-indazole-3-carboxamide |
| 19 | 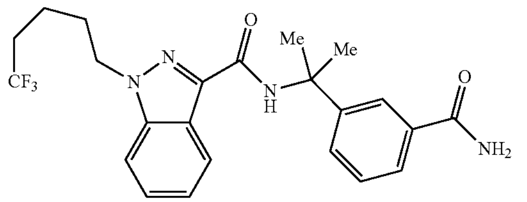 [SMILES: CC(C)(NC(=O)c1nn(CCCCC(F)(F)F)c2ccccc12)c1cccc(C(N)=O)c1] | N-[2-(3-carbamoylphenyl)propan-2-yl]-1-(5,5,5-trifluoropentyl)-1H-indazole-3-carboxamide |

TABLE 1-continued

| Synthetic Examples | | |
|---|---|---|
| Example # | Structure | Name |
| 20 | 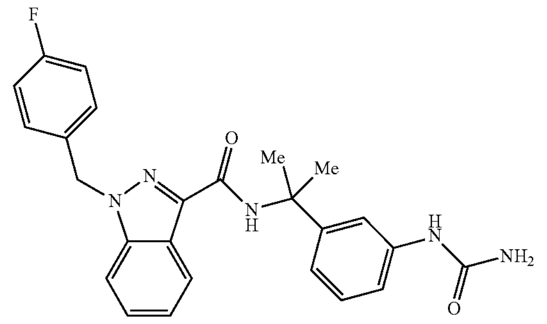 [SMILES: CC(C)(NC(=O)c1nn(Cc2ccc(F)cc2)c2ccccc12)c1cccc(NC(N)=O)c1] | N-[2-(3-acetamidophenyl)propan-2-yl]-1-[(4-fluorophenyl)methyl]-1H-indazole-3-carboxamide |
| 21 | 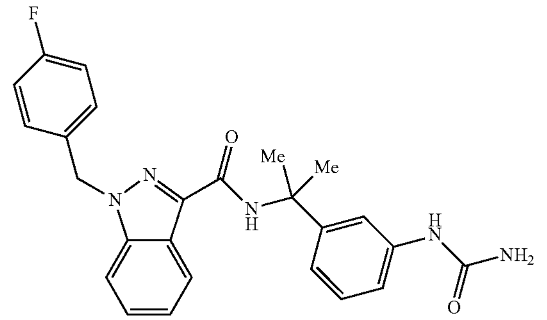 [SMILES: CC(C)(NC(=O)c1nn(Cc2ccc(F)cc2)c2ccccc12)c1cccc(NC(N)=O)c1] | N-{2-[3-(carbamoylamino)phenyl]propan-2-yl}-1-[(4-fluorophenyl)methyl]-1H-indazole-3-carboxamide |
| 22 | 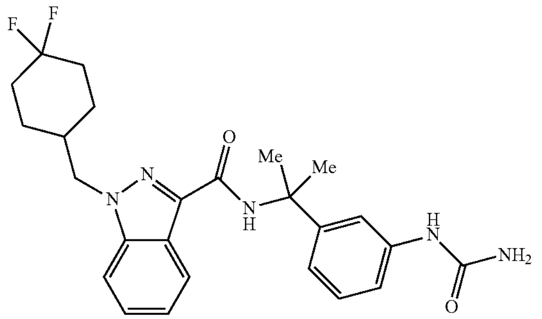 [SMILES: CC(C)(NC(=O)c1nn(CC2CCC(F)(F)CC2)c2ccccc12)c1cccc(NC(N)=O)c1] | N-{2-[3-(carbamoylamino)phenyl]propan-2-yl}-1-[(4,4-difluorocyclohexyl)methyl]-1H-indazole-3-carboxamide |
| 23 | 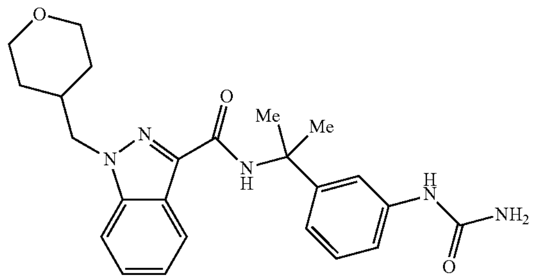 [SMILES: CC(C)(NC(=O)c1nn(CC2CCOCC2)c2ccccc12)c1cccc(NC(N)=O)c1] | N-{2-[3-(carbamoylamino)phenyl]propan-2-yl}-1-(oxan-4-ylmethyl)-1H-indazole-3-carboxamide |
| 24 | 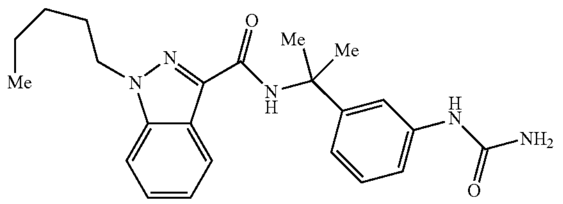 [SMILES: CCCCCn1nc(C(=O)NC(C)(C)c2cccc(NC(N)=O)c2)c2ccccc21] | N-{2-[3-(carbamoylamino)phenyl]propan-2-yl}-1-pentyl-1H-indazole-3-carboxamide |

TABLE 1-continued

Synthetic Examples

| Example # | Structure | Name |
|---|---|---|
| 25 | 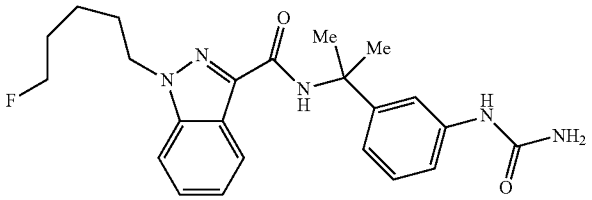 [SMILES: CC(C)(NC(=O)c1nn(CCCCCF)c2ccccc12)c1cccc(NC(N)=O)c1] | N-{2-[3-(carbamoylamino)phenyl]propan-2-yl}-1-(5-fluoropentyl)-1H-indazole-3-carboxamide |
| 26 | 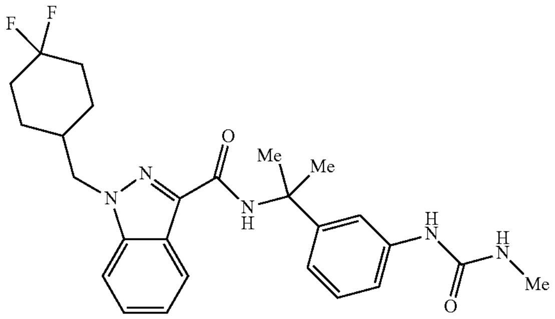 [SMILES: CNC(=O)Nc1cccc(C(C)(C)NC(=O)c2nn(CC3CCC(F)(F)CC3)c3ccccc23)c1] | 1-[(4,4-difluorocyclohexyl)methyl]-N-(2-{3-[(methylcarbamoyl)amino]phenyl}propan-2-yl)-1H-indazole-3-carboxamide |
| 27 | 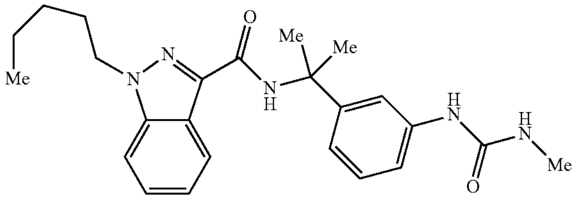 [SMILES: CCCCCn1nc(C(=O)NC(C)(C)c2cccc(NC(=O)NC)c2)c2ccccc21] | N-(2-{3-[(methylcarbamoyl)amino]phenyl}propan-2-yl)-1-pentyl-1H-indazole-3-carboxamide |
| 28 | 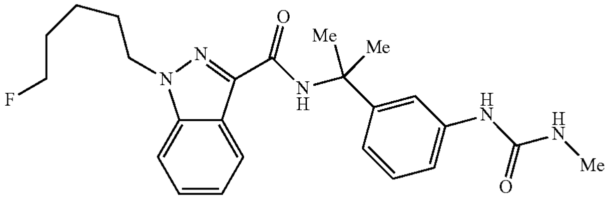 [SMILES: CNC(=O)Nc1cccc(C(C)(C)NC(=O)c2nn(CCCCCF)c3ccccc23)c1] | 1-(5-fluoropenty])-N-(2-{3-[(methylcarbamoyl)amino]phenyl}propan-2-yl)-1H-indazole-3-carboxamide |
| 29 | 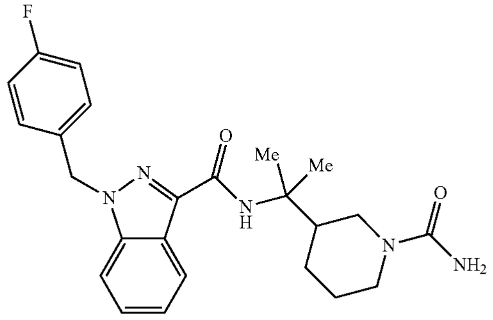 [SMILES: CC(C)(NC(=O)c1nn(Cc2ccc(F)cc2)c2ccccc12)C1CCCN(C(N)=O)C1] | N-[2-(1-carbamoylpiperidin-3-yl)propan-2-yl]-1-[(4-fluorophenyl)methyl]-1H-indazole-3-carboxamide |

TABLE 1-continued

| Synthetic Examples | | |
|---|---|---|
| Example # | Structure | Name |
| 30 | 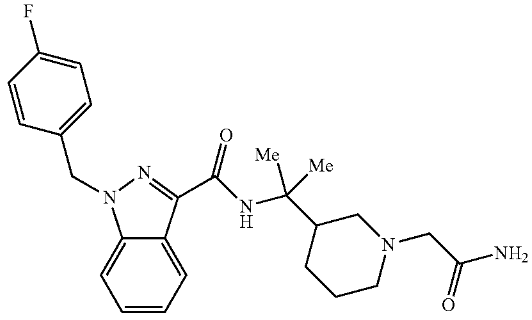 [SMILES: CC(C)(NC(=O)c1nn(Cc2ccc(F)cc2)c2ccccc12)C1CCCN(CC(N)=O)C1] | N-{2-[1-(carbamoylmethyl)piperidin-3-yl]propan-2-yl}-1-[(4-fluorophenyl)methyl]-1H-indazole-3-carboxamide |
| 31 | 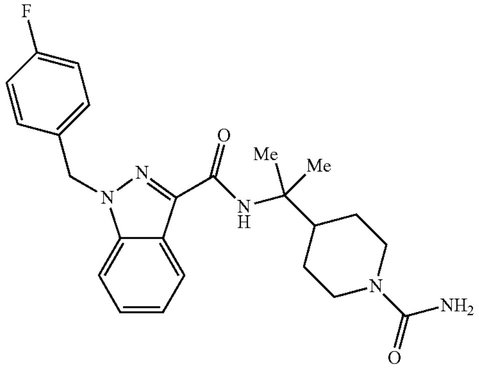 [SMILES: CC(C)(NC(=O)c1nn(Cc2ccc(F)cc2)c2ccccc12)C1CCN(C(N)=O)CC1] | N-[2-(1-carbamoylpiperidin-4-yl)propan-2-yl]-1-[(4-fluorophenyl)methyl]-1H-indazole-3-carboxamide |
| 32 | 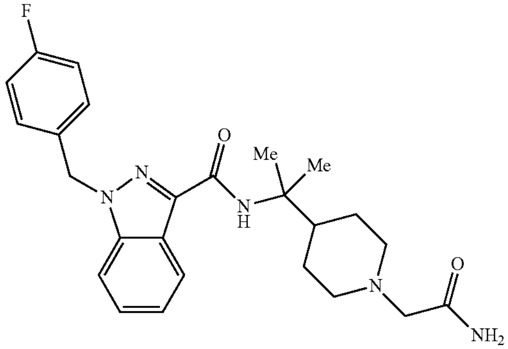 [SMILES: CC(C)(NC(=O)c1nn(Cc2ccc(F)cc2)c2ccccc12)C1CCN(CC(N)=O)CC1] | N-{2-[1-(carbamoylmethyl)piperidin-4-yl]propan-2-yl}-1-[(4-fluorophenyl)methyl]-1H-indazole-3-carboxamide |
| 33 | 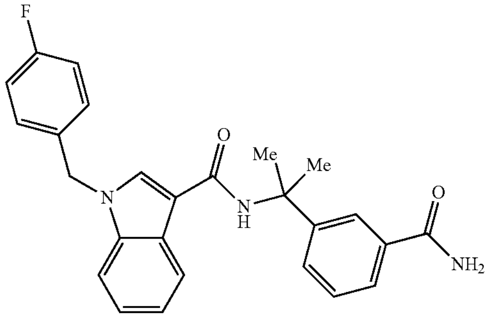 [SMILES: CC(C)(NC(=O)c1cn(Cc2ccc(F)cc2)c2ccccc12)c1cccc(C(N)=O)c1] | N-[2-(3-carbamoylphenyl)propan-2-yl]-1-[(4-fluorophenyl)methyl]-1H-indole-3-carboxamide |

The present disclosure includes pharmaceutically acceptable salt forms of the exemplified compounds.

Abbreviations: As used herein the symbols and conventions used in these processes, schemes and examples are consistent with those used in the contemporary scientific literature, for example, the *Journal of the American Chemical Society* or the *Journal of Biological Chemistry*. Specifically, the following abbreviations may be used:

| | |
|---|---|
| g (grams); | mg (milligrams); |
| L (liters); | mL (milliliters); |
| μL (microliters); | psi (pounds per square inch); |
| M (molar); | mM (millimolar); |
| Hz (Hertz); | MHz (megahertz); |
| mol (moles); | mmol (millimoles); |
| RT or rt (room temperature); | hr (hours); |
| min (minutes); | TLC (thin layer chromatography); |
| mp (melting point); | RP (reverse phase); |
| $T_r$ (retention time); | TFA (trifluoroacetic acid); |
| TEA (triethylamine); | THF (tetrahydrofuran); |
| TFAA (trifluoroacetic anhydride); | $CD_3OD$ (deuterated methanol); |
| $CDCl_3$ (deuterated chloroform); | DMSO (dimethylsulfoxide); |
| $SiO_2$ (silica gel); | atm (atmosphere); |
| EtOAc (ethyl acetate); | $CHCl_3$ (chloroform); |
| HCl (hydrochloric acid); | Ac (acetyl); |
| DMF (N,N-dimethylformamide); | Me (methyl); |
| $Cs_2CO_3$ (cesium carbonate); | EtOH (ethanol); |
| Et (ethyl); | t-Bu (tert-butyl); |
| MeOH (methanol) | p-TsOH (p-toluenesulfonic acid); |
| DCM (dichloromethane) | DCE (dichloroethane) |
| $Et_2O$ (diethyl ether) | $K_2CO_3$ (potassium carbonate); |
| $Na_2CO_3$ (sodium carbonate); | i-PrOH (isopropyl alcohol) |
| $NaHCO_3$ (sodium bicarbonate); | ACN (acetonitrile); |
| Pr (propyl); | i-Pr (isopropyl); |
| PE (petroleum ether); | Hex (hexanes); |
| $H_2SO_4$ (sulfuric acid); | HCl (hydrochloric acid); |
| $Et_3N$ (triethylamine); | $Na_2SO_4$ (sodium sulfate); |
| MTBE (methyl tert-butyl ether); | Boc (tert-butoxycarbonyl); |
| DIPEA (diisopropylethylamine); | IPA (isopropanol); |
| HMDS (hexamethyldisilazane) | $NH_4Cl$ (ammonium chloride) |
| $NH_4CO_3$ (ammonium carbonate) | $MgSO_4$ (magnesium sulfate) |
| $NH_4OH$ (ammonium hydroxide) | |

Chemistry General.

Purity and characterization of compounds were established by a combination of LC/MS, NMR, HPLC and TLC analytical techniques, as described below. $^1$H spectra were recorded on a Bruker Avance DPX-300 (300 MHz) spectrometer and were determined in chloroform-d (7.26 ppm) or methanol-$d_4$ (3.31 ppm) with tetramethylsilane (TMS, 0.00 ppm) as the internal reference unless otherwise noted. Chemical shifts are reported in ppm relative to the TMS signal and coupling constant (J) values are reported in hertz (Hz). Thin-layer chromatography (TLC) was performed on precoated silica gel 60 F254 plates. TLC spots were visualized with UV light or 12 detection.

LC/MS was performed with an Agilent InfinityLab MSD single quadrupole mass spectrometer equipped with an API-ES and an Agilent Infinity II 1260 HPLC equipped with an Agilent Infinity 1260 variable wavelength detector and a Phenomenex Synergi 2.5 □m Hydro-RP 100A C18 30×2 mm column. HPLC Method: starting with a flow rate of 0.6 mL/min for 0.4 minutes at 20% solvent B followed by a 1.3 minute gradient of 20-95% solvent B at 0.6 mL/min followed by 2 minutes at 95% solvent B with a flow rate of 0.6 mL/min for 0.3 minutes and then a gradual ramp up of the flow rate to 1.2 mL/min at the end (solvent A, water with 0.1% formic acid; solvent B, acetonitrile with 0.1% formic acid and 5% water; absorbance monitored at 220 and 280 nm). MS Method: using atmospheric pressure ionization-electrospray, positive and negative ions were monitored in the range of 70-700.

Unless stated otherwise, all test compounds were at least 95% pure as determined by HPLC. HPLC method: a Waters 2695 Separation Module equipped with a Waters 2996 Photodiode Array Detector and a Phenomenex Synergi 4 μm Hydro-RP 80A C18 250×4.6 mm column using a flow rate of 1 mL/min starting with 1 min at 5% solvent B, followed by a 15 min gradient of 5-95% solvent B, followed by 9 min at 95% solvent B (solvent A, water with 0.1% TFA; solvent B, acetonitrile with 0.1% TFA and 5% water; absorbance monitored at 220 and 280 nm).

General Procedure A: N-Alkylation of Indazoles 1 or Analogous Indoles. A mixture of an indazole 1 (4 mmol) or an analogous indole, an alkyl bromide (2.2 mmol, 1.1 equiv), $K_2CO_3$ (1.7 g, 3 equiv) and MeCN (6 mL) was stirred at rt for 15 min and then at 60° C. for 15 h for indazoles and 70° C. for 15 h for indoles. Ethyl acetate (40 mL) was added, followed by water (8 mL) and brine (16 mL). After 10 min, the aqueous layer was removed. Celite (5 g) and toluene (4 mL) were added to the organic layer and the solvent evaporated. Flash chromatography using silica gel with an EtOAc/hexanes gradient provided the purified N-alkylated indazole or analogous indole.

General Procedure B: Hydrolysis of Indazole 3-Carboxy Methyl Esters or Analogous Indoles. To a solution of a N-alkyl indazole 3-carboxy methyl ester (3 mmol) or an analogous indole in dioxane (6 mL) was added 2 N NaOH (3 mL, 2 equiv). The resulting mixture was heated at 50° C. for 15 h for indazoles and 60° C. for 15 h for indoles. The mixture was acidified with 6 N HCl (1.1 mL, 2.1 equiv). Ethyl acetate (30 mL) was added, followed by brine (6 mL). The aqueous layer was saturated with sodium chloride and the layers were separated. The aqueous layer was extracted with ethyl acetate (1×3 mL). The combined organic layers was dried (sodium sulfate, 20 min) & filtered. Toluene (3 mL) was added and the solvent evaporated to provide the N-alkyl indazole 3-carboxylic acid 2 or an analogous indole.

General Procedure C: Indazole Amides 3 or Analogous Indoles. To a heterogeneous mixture of an N-alkyl indazole 3-carboxylic acid 2 (0.2 mmol) or an analogous indole, HBTU (84 mg, 1.1 equiv) and MeCN (1 mL) was added $NEt_3$ (0.061 mL, 2.2 equiv). The mixture was stirred at rt for 30 min. An amine (1.1 equiv) was added and after 30 min, the mixture was heated at 50° C. for 15 h. Water (0.8 mL) was added and after 5 min, EtOAc (3 mL) was added, followed by brine (0.8 mL). After 10 min, the aqueous layer was removed and the organic layer was washed with 0.5 M $NaHCO_3$ solution (0.8 mL). Celite (600 mg) was added to the organic layer and the solvent was evaporated. Flash chromatography using silica gel with an EtOAc/hexanes gradient provided the purified indazole amide 3 or an analogous indole.

General Procedure D: Aryl Nitriles from Aryl Bromides 4. Using low light and nitrogen, $Pd(PPh_3)_4$ (70 mg, 0.2 equiv) was added to a solution of an aryl bromide 4 (0.3 mmol) or an analogous indole and $Zn(CN)_2$ (110 mg, 3 equiv) in DMF (1 mL). The mixture was stirred at rt for 10 min and then heated at 70-75° C. for 20 h. Ethyl acetate (4 mL) was added, followed by water (1 mL) and then saturated $NaHCO_3$ solution (2 mL). After 10 mins, the aqueous layer was removed and the organic layer washed with brine (2×1 mL). Celite (800 mg) was added to the organic layer and the solvent was evaporated. Flash chromatography using silica gel with an EtOAc/hexanes gradient provided the purified nitrile.

General Procedure E: Aryl Carboxamides 5 from Aryl Nitriles. To a mixture of an aryl nitrile (0.2 mmol) in EtOH (0.8 mL) was added 50% $H_2O_2$ (0.2 mL) followed by 6 N NaOH (0.2 mL). The mixture was vigorously stirred at rt for 20 h. Ethyl acetate (3 mL) was added, followed by brine (0.6 mL). After 10 min, the aqueous layer was removed, celite (500 mg) was added to the organic layer and the solvent evaporated. Flash chromatography using silica gel with an EtOAc/hexanes gradient containing up to 4% MeOH provided the purified aryl carboxamide 5.

General Procedure F: Aryl Carboxamides 5 from Aryl Bromides 4. To a solution of an aryl bromide 4 (0.2 mmol) in THF (1 mL) at −78° C. (IPA/dry ice bath) was added dw 2.5 M n-BuLi in hexanes (0.16 mL, 2 equiv). After 5 min, TMS-NCO (0.041 mL, 1.5 equiv) was added all at once. After 1 h, 2 N HCl (0.24 mL) was added dw and then the bath was removed. The mixture was stirred at rt for 30 min. Ethyl acetate (3 mL) was added, followed by brine (0.6 mL). After 10 min, the aqueous layer was removed, celite (600 mg) was added to the organic layer and the solvent was evaporated. Flash chromatography using silica gel with an EtOAc/hexanes gradient containing up to 4% MeOH provided the purified aryl carboxamide 5.

General Procedure G: Deprotection of Boc Piperidines 6. To a mixture of a Boc protected piperidine 6 (0.2 mmol) and ethanol (1 mL) was added 6 N HCl (0.5 mL). The mixture was stirred at rt for 10 min and then at 55° C. for 15 h. Chloroform (3 mL) was added, followed by brine (0.5 mL) and then slow addition of 6 N NaOH (0.55 mL). After 10 min, the organic and aqueous layers were separated. The aqueous layer was saturated with NaCl and extracted with $CHCl_3$ (2×1 mL). The combined organic layers was dried ($Na_2SO_4$ for 20 min) and filtered. Toluene (1 mL) was added and the solvent evaporated, providing the deprotected piperidine.

General Procedure H: Reaction of Piperidines with TMS-NCO. To a solution of a piperidine (0.15 mmol) in DCE (1 mL) was added TMS-NCO (0.025 mL, 1.2 equiv). The mixture was stirred at rt for 15 h. Water (0.1 mL) and EtOAc (1 mL) were added. After 15 min, celite (600 mg) was added and the solvent evaporated. Flash chromatography using silica gel with an EtOAc/hexanes gradient containing up to 6% MeOH provided the purified piperidine urea 7.

General Procedure I: Alkylation of Piperidines with Chloroacetamide. A mixture of a piperidine (0.2 mmol), chloroacetamide (23 mg, 1.2 equiv), $K_2CO_3$ (83 mg, 3 equiv) and MeCN (1 mL) was stirred at rt for 15 min and then heated at 50° C. for 15 h. EtOAc (3 mL) was added, followed by water (0.8 mL) and then brine (0.8 mL). After 10 min, the aqueous layer was removed, celite (600 mg) was added and the solvent evaporated. Flash chromatography using silica gel with an EtOAc/hexanes gradient containing up to 8% MeOH provided the purified carboxamide 7.

General Procedure J: Reaction of Anilines 5 with TMS-NCO. To a solution of an aniline 8 (0.15 mmol) in DCE (1 mL) was added TMS-NCO (0.025 mL, 1.2 equiv). The mixture was stirred at rt for 1 h and then at 60° C. for 20 h. Water (0.1 mL), MeOH (0.1 mL) and EtOAc (1 mL) were added. After 15 min, celite (600 mg) was added and the solvent evaporated. Flash chromatography using silica gel with an EtOAc/hexanes gradient containing up to 4% MeOH provided the purified aryl urea 9.

General Procedure K: Reaction of Anilines 8 with Acid Chlorides or Chloroformates. To a solution of an aniline 8 (0.15 mmol) in DCE (1 mL) was added an acid chloride or chloroformate (1.2 equiv) followed by pyridine (0.18 mL, 1.5 equiv). The mixture was stirred at rt for 15 h. EtOAc (3 mL) was added, followed by water (0.8 mL) and then brine (0.8 mL). After 10 min, the aqueous layer was removed and the organic layer washed with 0.5 M $NaHCO_3$ solution (0.6 mL). Celite (600 mg) was added to the organic layer and the solvent evaporated. Flash chromatography using silica gel with an EtOAc/hexanes gradient containing up to 4% MeOH provided the purified aryl amide or urea 9.

Synthetic Examples

N-[(1R)-1-(3-Carbamoylphenyl)ethyl]-1-[(4-fluorophenyl)methyl]-1H-indazole-3-carboxamide (Example 10). The title compound was prepared by the general procedure E to provide 25 mg (95%) of a white amorphous solid. $R_f$=0.22 (2% MeOH/60% EtOAc/hexanes; UV active). $^1H$ NMR (300 MHz, $CDCl_3$) δ 8.35 (d, J=8.1 Hz, 1H), 7.93 (s, 1H), 7.68 (d, J=7.5 Hz, 1H), 7.61 (d, J=7.5 Hz, 1H), 7.28-7.48 (m, 5H), 7.11-7.21 (m, 2H), 6.94-7.07 (m, 2H), 5.57 (s, 2H), 5.27-5.48 (m, 1H), 1.65 (d, J=7.0 Hz, 3H). LC/MS (m/z) 417.4 (M+1), >97% at 2.50 min. HPLC>98% at 14.60 min.

N-[(1S)-1-(3-Carbamoylphenyl)ethyl]-1-[(4-fluorophenyl)methyl]-1H-indazole-3-carboxamide (Example 11). The title compound was prepared by the general procedure E to provide 13 mg (82%) of a white amorphous solid. $R_f$=0.22 (2% MeOH/60% EtOAc/hexanes; UV active). $^1H$ NMR (300 MHz, $CDCl_3$) δ 8.35 (d, J=8.1 Hz, 1H), 7.93 (s, 1H), 7.68 (d, J=7.5 Hz, 1H), 7.60 (d, J=7.5 Hz, 1H), 7.28-7.49 (m, 5H), 7.10-7.20 (m, 2H), 6.92-7.07 (m, 2H), 5.56 (s, 2H), 5.27-5.48 (m, 1H), 1.65 (d, J=7.0 Hz, 3H). LC/MS (m/z) 417.4 (M+1), >97% at 2.50 min. HPLC 99% at 14.60 min.

N-[2-(3-Carbamoylphenyl)propan-2-yl]-1-[(4-fluorophenyl)methyl]-1H-indazole-3-carboxamide (Example 12). The title compound was prepared by the general procedure E to provide 87 mg (84%) of a white crystalline solid. $R_f$=0.27 (2% MeOH/60% EtOAc/hexanes; UV active). $^1H$ NMR (300 MHz, $CDCl_3$) δ 8.28 (d, J=8.1 Hz, 1H), 8.00 (s, 1H), 7.65 (d, J=7.5 Hz, 1H), 7.59 (d, J=7.4 Hz, 1H), 7.46 (s, 1H), 7.28-7.41 (m, 3H), 7.13-7.25 (m, 3H), 6.95-7.08 (m, 2H), 5.58 (s, 2H), 1.85 (s, 6H). LC/MS (m/z) 431.4 (M+1), >98% at 2.54 min. HPLC>98% at 15.12 min.

N-[2-(3-Carbamoylphenyl)propan-2-yl]-1-[(2,4-difluorophenyl)methyl]-1H-indazole-3-carboxamide (Example 13). The title compound was prepared by the general procedure E to provide 104 mg (77%) of a white crystalline solid. $R_f$=0.26 (2% MeOH/60% EtOAc/hexanes; UV active). $^1H$ NMR (300 MHz, $CDCl_3$) δ 8.31 (d, J=8.3 Hz, 1H), 8.02 (s, 1H), 7.69 (d, J=7.8 Hz, 1H), 7.62 (d, J=7.3 Hz, 1H), 7.37-7.48 (m, 4H), 7.21-7.27 (m, 1H), 7.02-7.11 (m, 1H), 6.76-6.94 (m, 2H), 6.20 (br s, 1H), 5.72 (br s, 1H), 5.64 (s, 3H), 1.88 (s, 6H). LC/MS (m/z) 449.0 (M+1), >98% at 2.73 min. HPLC 99% at 15.34 min.

N-[2-(3-Carbamoylphenyl)propan-2-yl]-1-[1-(4-fluorophenyl)ethyl]-1H-indazole-3-carboxamide (Example 14). The title compound was prepared by the general procedure E to provide 32 mg (83%) of a white crystalline solid. $R_f$=0.40 (2% MeOH/60% EtOAc/hexanes; UV active). $^1H$ NMR (300 MHz, $CDCl_3$) δ 8.27 (d, J=8.1 Hz, 1H), 8.02 (s, 1H), 7.68 (d, J=7.7 Hz, 1H), 7.61 (d, J=7.4 Hz, 1H), 7.48 (s, 1H), 7.37 (t, J=7.7 Hz, 1H), 7.17-7.31 (m, 5H), 7.01 (t, J=8.6 Hz, 2H), 6.46 (br s, 1H), 5.85 (q, J=6.8 Hz, 2H), 2.50 (br s, 1H), 2.06 (d, J=7.0 Hz, 3H), 1.80-1.95 (m, 6H). LC/MS (m/z) 445.0 (M+1), 489.2 (M−1+$HCO_2H$), >98% at 2.75 min. HPLC>99% at 15.70 min.

N-[2-(3-Carbamoylphenyl)propan-2-yl]-1-[(4,4-difluorocyclohexyl)methyl]-1H-indazole-3-carboxamide (Example 15). The title compound was prepared by the general procedure F to provide 47 mg (43%) of a white crystalline solid. $R_f$=0.19 (2% MeOH/60% EtOAc/hexanes; UV active). $^1H$ NMR (300 MHz, $CDCl_3$) δ 8.26 (d, J=8.1 Hz, 1H), 8.00 (s, 1H), 7.66 (d, J=7.9 Hz, 1H), 7.60 (d, J=7.7 Hz, 1H), 7.32-7.47 (m, 4H), 7.16-7.25 (m, 1H), 4.28 (d, J=7.4 Hz, 2H), 2.06-2.26 (m, 3H), 1.86 (s, 6H), 1.57-1.78 (m, 4H), 1.21-1.55 (m, 4H). LC/MS (m/z) 455.0 (M+1), 499.0 (M−1+$HCO_2H$), >98% at 2.73 min. HPLC>99% at 15.34 min.

N-[2-(3-Carbamoylphenyl)propan-2-yl]-1-(oxan-4-ylmethyl)-1H-indazole-3-carboxamide (Example 16). The title compound was prepared by the general procedure E to provide 31 mg (62%) of a white crystalline solid. $R_f$=0.14 (2% MeOH/70% EtOAc/hexanes; UV active). $^1H$ NMR (300 MHz, $CDCl_3$) δ 8.27 (d, J=8.1 Hz, 1H), 8.00 (s, 1H), 7.67 (d, J=7.9 Hz, 1H), 7.60 (d, J=7.5 Hz, 1H), 7.33-7.49 (m, 4H), 7.15-7.24 (m, 1H), 4.28 (d, J=7.2 Hz, 2H), 3.91-4.05 (m, 2H), 3.25-3.47 (m, 2H), 2.25-2.41 (m, 1H), 1.87 (s, 6H), 1.42-1.59 (m, 4H). LC/MS (m/z) 421.0 (M+1), 465.2 (M−1+$HCO_2H$), >98% at 2.56 min. HPLC>99% at 13.38 min.

N-[2-(3-Carbamoylphenyl)propan-2-yl]-1-pentyl-1H-indazole-3-carboxamide (Example 17). The title compound was prepared by the general procedure F to provide 34 mg (48%) of a white amorphous solid. $R_f$=0.28 (2% MeOH/60% EtOAc/hexanes; UV active). $^1H$ NMR (300 MHz, $CDCl_3$) δ 8.26 (d, J=8.3 Hz, 1H), 7.98 (s, 1H), 7.68 (d, J=7.7 Hz, 1H), 7.61 (d, J=7.5 Hz, 1H), 7.33-7.48 (m, 4H), 7.16-7.24 (m, 1H), 4.39 (t, J=7.2 Hz, 2H), 1.92-2.04 (m, 2H), 1.86 (s, 6H), 1.28-1.45 (m, 4H), 0.92 (t, J=6.7 Hz, 3H). LC/MS (m/z) 393.0 (M+1), >98% at 2.78 min. HPLC 99% at 16.21 min.

N-[2-(3-Carbamoylphenyl)propan-2-yl]-1-(5-fluoropentyl)-1H-indazole-3-carboxamide (Example 18). The title compound was prepared by the general procedure F to provide 34 mg (30%) of a white amorphous solid. $R_f$=0.18 (2% MeOH/60% EtOAc/hexanes; UV active). $^1H$ NMR (300 MHz, $CDCl_3$) δ 8.27 (d, J=8.1 Hz, 1H), 7.98 (s, 1H), 7.68 (d, J=7.7 Hz, 1H), 7.61 (d, J=7.4 Hz, 1H), 7.33-7.47 (m, 4H), 7.15-7.24 (m, 1H), 4.53 (t, J=5.8 Hz, 1H), 4.34-4.47 (m, 3H), 1.96-2.12 (m, 2H), 1.87 (s, 6H), 1.25-1.80 (m, 6H). LC/MS (m/z) 411.0 (M+1), 455.2 (M−1+$HCO_2H$), >97% at 2.68 min. HPLC 99% at 14.66 min.

N-[2-(3-Carbamoylphenyl)propan-2-yl]-1-(5,5,5-trifluoropentyl)-1H-indazole-3-carboxamide (Example 19). The title compound was prepared by the general procedure F to provide 14 mg (12%) of a white amorphous solid. $R_f$=0.21 (2% MeOH/60% EtOAc/hexanes; UV active). $^1H$ NMR (300 MHz, $CDCl_3$, $CD_3OD$) δ 8.23 (d, J=8.1 Hz, 1H), 7.94 (s, 1H), 7.66 (d, J=7.7 Hz, 2H), 7.36-7.46 (m, 3H), 7.19-7.27 (m, 1H), 4.45 (t, J=6.9 Hz, 2H), 2.01-2.25 (m, 4H), 1.86 (s, 6H), 1.57-1.70 (m, 2H). LC/MS (m/z) 447.0 (M+1), 491.0 (M−1+$HCO_2H$), >98% at 2.72 min. HPLC 99% at 14.93 min.

N-[2-(3-Acetamidophenyl)propan-2-yl]-1-[(4-fluorophenyl)methyl]-1H-indazole-3-carboxamide (Example 20). The title compound was prepared by the general procedure K to provide 21 mg (91%) of a white crystalline solid. $R_f$=0.38 (2% MeOH/60% EtOAc/hexanes; UV active). $^1H$ NMR (300 MHz, $CDCl_3$) δ 8.31 (d, J=7.7 Hz, 1H), 7.57 (br s, 1H), 7.28-7.50 (m, 6H), 7.11-7.24 (m, 4H), 6.95-7.09 (m, 2H), 5.59 (s, 2H), 2.05 (s, 3H), 1.81 (s, 6H). LC/MS (m/z) 445.0 (M+1), 489.2 (M−1+$HCO_2H$), >98% at 2.75 min. HPLC>99% at 15.58 min.

N-{2-[3-(Carbamoylamino)phenyl]propan-2-yl}-1-[(4-fluorophenyl)methyl]-1H-indazole-3-carboxamide (Example 21). The title compound was prepared by the general procedure J to provide 56 mg (63%) of a white crystalline solid. $R_f$=0.38 (5% MeOH/65% EtOAc/hexanes; UV active). $^1H$ NMR (300 MHz, $CDCl_3$, $CD_3OD$) δ 8.24 (d, J=8.1 Hz, 1H), 7.54 (s, 1H), 7.31-7.43 (m, 3H), 7.14-7.27 (m, 5H), 6.97-7.10 (m, 2H), 5.60 (s, 2H), 1.80 (s, 6H). LC/MS (m/z) 446.0 (M+1), 490.2 (M−1+$HCO_2H$), >98% at 2.70 min. HPLC>99% at 14.99 min.

N-{2-[3-(Carbamoylamino)phenyl]propan-2-yl}-1-[(4,4-difluorocyclohexyl)methyl]-1H-indazole-3-carboxamide (Example 22). The title compound was prepared by the general procedure J to provide 33 mg (54%) of a white crystalline solid. $R_f$=0.14 (2% MeOH/60% EtOAc/hexanes; UV active). $^1H$ NMR (300 MHz, $CDCl_3$, $CD_3OD$) δ 8.23 (d, J=7.9 Hz, 1H), 7.50 (s, 1H), 7.32-7.44 (m, 2H), 7.14-7.28 (m, 4H), 4.30 (d, J=6.8 Hz, 2H), 2.07-2.19 (m, 2H), 1.82 (s, 6H), 1.59-1.80 (m, 4H), 1.38-1.56 (m, 2H), 1.21-1.35 (m, 1H). LC/MS (m/z) 470.0 (M+1), 514.2 (M−1+$HCO_2H$), >98% at 2.74 min. HPLC 99% at 14.83 min.

N-{2-[3-(Carbamoylamino)phenyl]propan-2-yl}-1-(oxan-4-ylmethyl)-1H-indazole-3-carboxamide (Example 23). The title compound was prepared by the general procedure J to provide 49 mg (100%) of a white crystalline solid. $R_f$=0.15 (5% MeOH/65% EtOAc/hexanes; UV active). $^1H$ NMR (300 MHz, $CDCl_3$, $CD_3OD$) δ 8.23 (d, J=8.3 Hz, 1H), 7.38-7.48 (m, 2H), 7.36 (s, 1H), 7.16-7.28 (m, 4H), 4.29 (d, J=7.0 Hz, 2H), 3.91-4.06 (m, 2H), 3.33-3.45 (m, 2H), 1.83 (s, 6H), 1.43-1.60 (m, 4H), 0.64-0.88 (m, 1H). LC/MS (m/z) 436.0 (M+1), 480.2 (M−1+$HCO_2H$), >98% at 2.57 min. HPLC>99% at 12.82 min.

N-{2-[3-(Carbamoylamino)phenyl]propan-2-yl}-1-pentyl-1H-indazole-3-carboxamide (Example 24). The title compound was prepared by the general procedure J to provide 16 mg (51%) of a white crystalline solid. $R_f$=0.17 (2% MeOH/60% EtOAc/hexanes; UV active). $^1H$ NMR (300 MHz, $CDCl_3$, $CD_3OD$) δ 8.20 (d, J=8.1 Hz, 1H), 7.32-7.47 (m, 3H), 7.11-7.27 (m, 4H), 4.40 (t, J=7.2 Hz, 2H), 1.91-2.07 (m, 2H), 1.77 (s, 6H), 1.20-1.44 (m, 4H), 0.92 (t, J=6.6 Hz, 3H). LC/MS (m/z) 408.0 (M+1), 452.2 (M−1+$HCO_2H$), >98% at 2.77 min. HPLC 99% at 15.73 min.

N-{2-[3-(Carbamoylamino)phenyl]propan-2-yl}-1-pentyl-1H-indazole-3-carboxamide (Example 25). The title compound was prepared by the general procedure J to provide 24 mg (77%) of a white crystalline solid. $R_f$=0.13 (2% MeOH/60% EtOAc/hexanes; UV active). $^1H$ NMR (300 MHz, $CDCl_3$, $CD_3OD$) δ 8.20 (d, J=8.3 Hz, 1H), 7.34-7.49 (m, 3H), 7.16-7.28 (m, 4H), 4.54 (t, J=5.8 Hz, 1H), 4.32-4.48 (m, 3H), 1.95-2.12 (m, 2H), 1.67-1.87 (m, 8H), 1.44-1.57 (m, 2H). LC/MS (m/z) 426.0 (M+1), 470.2 (M−1+$HCO_2H$), >98% at 2.68 min. HPLC>98% at 14.15 min.

1-[(4,4-Difluorocyclohexyl)methyl]-N-(2-{3-[(methylcarbamoyl)amino]phenyl}propan-2-yl)-1H-indazole-3-carboxamide (Example 26). The title compound was prepared by the general procedure K to provide 30 mg (48%) of a white amorphous solid. $R_f$=0.22 (2% MeOH/60% EtOAc/hexanes; UV active). $^1H$ NMR (300 MHz, $CDCl_3$) δ 8.24 (d, J=8.1 Hz, 1H), 7.56 (s, 1H), 7.49 (s, 1H), 7.36-7.44 (m, 2H), 7.22 (dt, J=8.1, 3.9 Hz, 1H), 7.02-7.15 (m, 3H), 6.71-6.84 (m, 2H), 4.30 (d, J=7.2 Hz, 2H), 2.61 (s, 3H), 2.07-2.23 (m, 2H), 1.62-1.89 (m, 10H), 1.37-1.56 (m, 2H), 1.19-1.31 (m, 1H). LC/MS (m/z) 484.0 (M+1), 528.2 (M−1+$HCO_2H$), >98% at 2.76 min. HPLC>98% at 15.38 min.

N-(2-{3-[(Methylcarbamoyl)amino]phenyl}propan-2-yl)-1-pentyl-1H-indazole-3-carboxamide (Example 27). The title compound was prepared by the general procedure K to provide 9 mg (28%) of a colorless residue. $R_f$=0.24 (2% MeOH/60% EtOAc/hexanes; UV active). $^1H$ NMR (300 MHz, $CDCl_3$) δ 8.23 (d, J=8.1 Hz, 1H), 7.49-7.59 (m, 1H), 7.33-7.49 (m, 3H), 7.03-7.24 (m, 3H), 6.84-6.99 (m, 2H), 4.41 (t, J=7.2 Hz, 2H), 2.59 (s, 3H), 1.93-2.04 (m, 2H), 1.75 (s, 6H), 1.21-1.45 (m, 4H), 0.92 (t, J=6.8 Hz, 3H). LC/MS (m/z) 422.2 (M+1), 466.2 (M−1+$HCO_2H$), >97% at 2.81 min. HPLC 95% at 16.30 min.

1-(5-Fluoropentyl)-N-(2-{3-[(methylcarbamoyl)amino]phenyl}propan-2-yl)-1H-indazole-3-carboxamide (Example 28). The title compound was prepared by the general procedure K to provide 11 mg (34%) of a colorless residue. $R_f$=0.19 (2% MeOH/60% EtOAc/hexanes; UV active). $^1$H NMR (300 MHz, $CDCl_3$) δ 8.23 (d, J=8.1 Hz, 1H), 7.35-7.58 (m, 4H), 7.05-7.25 (m, 3H), 6.81-6.93 (m, 2H), 4.54 (t, J=5.8 Hz, 1H), 4.32-4.49 (m, 3H), 2.59 (s, 3H), 1.96-2.14 (m, 2H), 1.69-1.86 (m, 8H), 1.45-1.58 (m, 2H). LC/MS (m/z) 440.0 (M+1), 484.2 (M−1+$HCO_2$H), >97% at 2.74 min. HPLC 96% at 14.68 min.

N-[2-(1-Carbamoylpiperidin-3-yl)propan-2-yl]-1-[(4-fluorophenyl)methyl]-1H-indazole-3-carboxamide (Example 29). The title compound was prepared by the general procedure H to provide 51 mg (78%) of a white crystalline solid. $R_f$=0.19 (5% MeOH/65% EtOAc/hexanes; UV active). $^1$H NMR (300 MHz, $CDCl_3$) δ 8.33 (d, J=8.1 Hz, 1H), 7.28-7.43 (m, 3H), 7.11-7.22 (m, 2H), 6.96-7.08 (m, 2H), 6.89 (s, 1H), 5.57 (s, 2H), 4.61 (br s, 2H), 4.05-4.19 (m, 1H), 3.89-4.03 (m, 1H), 2.47-2.79 (m, 2H), 1.91-2.03 (m, 1H), 1.55-1.81 (m, 3H), 1.51 (s, 3H), 1.42 (s, 3H), 1.24-1.38 (m, 1H). LC/MS (m/z) 438.4 (M+1), >97% at 2.68 min. HPLC>99% at 15.37 min.

N-{2-[1-(Carbamoylmethyl)piperidin-3-yl]propan-2-yl}-1-[(4-fluorophenyl)methyl]-1H-indazole-3-carboxamide (Example 30). The title compound was prepared by the general procedure H to provide 54 mg (80%) of a white amorphous solid. $R_f$=0.19 (5% MeOH/65% EtOAc/hexanes; UV active). $^1$H NMR (300 MHz, $CDCl_3$) δ 8.36 (d, J=8.1 Hz, 1H), 7.28-7.43 (m, 2H), 7.09-7.23 (m, 3H), 6.88-7.07 (m, 3H), 5.56 (s, 2H), 5.32 (br s, 1H), 2.93-3.07 (m, 2H), 2.80-2.91 (m, 1H), 2.58-2.72 (m, 1H), 1.96-2.19 (m, 2H), 1.58-1.96 (m, 4H), 1.44 (s, 3H), 1.48 (s, 3H), 1.04-1.21 (m, 1H). LC/MS (m/z) 452.6 (M+1), >97% at 2.44 min. HPLC>99% at 12.94 min.

N-[2-(1-Carbamoylpiperidin-4-yl)propan-2-yl]-1-[(4-fluorophenyl)methyl]-1H-indazole-3-carboxamide (Example 31). The title compound was prepared by the general procedure H to provide 60 mg (92%) of a white amorphous solid. $R_f$=0.15 (5% MeOH/65% EtOAc/hexanes; UV active). $^1$H NMR (300 MHz, $CDCl_3$) δ 8.37 (d, J=7.9 Hz, 1H), 7.28-7.42 (m, 3H), 7.10-7.21 (m, 2H), 6.94-7.06 (m, 2H), 6.86 (s, 1H), 5.57 (s, 2H), 4.52 (br s, 2H), 3.95-4.07 (m, 2H), 2.75-2.91 (m, 2H), 2.45-2.61 (m, 1H), 1.73-1.84 (m, 3H), 1.45 (s, 6H), 1.26-1.41 (m, 1H). LC/MS (m/z) 438.4 (M+1), >97% at 2.66 min. HPLC>99% at 15.00 min.

N-{2-[1-(Carbamoylmethyl)piperidin-4-yl]propan-2-yl}-1-[(4-fluorophenyl)methyl]-1H-indazole-3-carboxamide (Example 32). The title compound was prepared by the general procedure I to provide 56 mg (83%) of a white crystalline solid. $R_f$=0.15 (5% MeOH/65% EtOAc/hexanes; UV active). $^1$H NMR (300 MHz, $CDCl_3$) δ 8.38 (d, J=8.1 Hz, 1H), 7.28-7.43 (m, 3H), 7.09-7.20 (m, 3H), 6.94-7.06 (m, 2H), 6.85 (s, 1H), 5.56 (s, 2H), 5.52 (br s, 1H), 2.87-3.07 (m, 4H), 2.14-2.36 (m, 2H), 1.72-1.84 (m, 3H), 1.37-1.54 (m, 8H). LC/MS (m/z) 452.6 (M+1), >97% at 2.42 min. HPLC>99% at 12.77 min.

N-[2-(3-Carbamoylphenyl)propan-2-yl]-1-[(4-fluorophenyl)methyl]-1H-indole-3-carboxamide (Example 33). The title compound was prepared by the general procedure E to provide 21 mg (80%) of an off white crystalline solid. $R_f$=0.28 (4% MeOH/66% EtOAc/hexanes; UV active). $^1$H NMR (300 MHz, $CDCl_3$, $CD_3OD$) δ 7.85-7.99 (m, 2H), 7.74 (s, 1H), 7.58-7.69 (m, 2H), 7.34-7.46 (m, 1H), 7.21-7.29 (m, 3H), 7.08-7.19 (m, 2H), 6.95-7.06 (m, 2H), 5.31 (s, 2H), 1.84 (s, 6H). LC/MS (m/z) 430.0 (M+1), 474.2 (M−1+46), >98% at 2.70 min. HPLC 99% at 14.28 min.

Biological Examples

In vitro cannabinoid receptor activity assay. Chinese Hamster Ovary (CHO) cells stably expressing either human CB1 or CB2 cDNA and the promiscuous G-protein Gαq16 were transferred to each well of a black Costar 96-well optical bottom plate (Corning Corporation). Each plate was incubated at 37° C. for 24 hr to confluence. The culture media was removed from the plates and cells were subsequently loaded with a fluorescent calcium probe (Calcium 5 dye, Molecular Devices) at a final loading concentration of 2 μM in a HBSS-based buffer containing 20 mM HEPES, 1% BSA and 10 μM Probenecid (Sigma) in a total volume of 225 μl. Cells were incubated at 37° C. for 1 hr and then stimulated with various concentrations of a test agent using a FLIPR Tetra plate-reader, which automatically added the agonist at 10× concentration to each well after reading baseline values for ~17 sec. Agonist-mediated change in fluorescence (488 nm excitation, 525 nm emission) was monitored in each well at 1 sec intervals for 60 sec and reported for each well. Data were analyzed using Prism software (GraphPad). Non-linear regression analysis was performed to fit data and obtain maximum response (Emax), effective concentration for 50% response (EC50), correlation coefficient (r2) and other parameters. All experiments were performed 3-6 times to ensure reproducibility.

Reference is made to the following reference, hereby incorporated by reference with regard to such assay, Seltzman, et al., *Peripherally Selective Cannabinoid 1 Receptor (CB1R) Agonists for the Treatment of Neuropathic Pain*, J Med Chem. 2016 Aug. 25; 59 (16):7525-43. doi: 10.1021/acs.jmedchem.6b00516. Epub 2016 Aug. 10.

In vitro binding affinity determination using radioligand displacement. Plasma membranes were isolated from HEK cells overexpressing either human CB1 or CB2. Binding was initiated with the addition of 40 μg of cell membrane proteins to assay tubes containing [3H]CP-55,940 (ca. 130 Ci/mmol), a test compound (for displacement studies), and a sufficient quantity of buffer (50 mM Tris-HCl, 1 mM EDTA, 3 mM MgCl2, 5 mg/mL BSA, pH 7.4) to bring the total incubation volume to 0.5 mL. Nonspecific binding was determined by the inclusion of 10 μM unlabeled CP-55,940. Following incubation at 30° C. for 1 h, binding was terminated by vacuum filtration through GF/C glass fiber filter plates. The filter plates were washed extensively and air-dried and sealed on the bottom. Liquid scintillate was added to the wells and the top sealed. After incubating the plates in cocktail for at least 2 h, the radioactivity present was determined by liquid scintillation spectrometry. Assays were done in duplicate, and results represent combined data from 3-6 experiments. Saturation and displacement data were analyzed by unweighted nonlinear regression of receptor binding data. For displacement studies, curve-fitting and IC50 calculation were done with GraphPad Prism (GraphPad Software, Inc., San Diego, CA).

Reference is made to the following reference, hereby incorporated by reference with regard to such assay, Zhang et al., *Synthesis and biological evaluation of bivalent ligands for the cannabinoid 1 receptor*, J Med Chem. 2010 Oct. 14; 53 (19):7048-60. doi: 10.1021/jm1006676.

Biological Data

TABLE 2

In Vitro Cannabinoid Receptor Activity of Select Compounds

| Example # | hCB1 Ca $EC_{50}$ (nM) Span[a] | hCB2 Ca $EC_{50}$ (nM) Span[a] | hCB1 $K_i$ (nM) | hCB2 $K_i$ (nM) |
|---|---|---|---|---|
| 10 | 490 | 660 | | |
| | 19% | 25% | | |
| 11 | 27 | 50 | 7 | 34 |
| | 86% | 48% | | |
| 12 | 21 | 27 | 4 | 10 |
| | 24% | 41% | | |
| 13 | 180 | 300 | 18 | 27 |
| | 32% | 19% | | |
| 14 | 240 | >10000 | | |
| | 76% | | | |
| 15 | 15 | 51 | | |
| | 86% | 38% | | |
| 16 | 140 | 63 | | |
| | 92% | 57% | | |
| 17 | 220 | 180 | | |
| | 24% | 43% | | |
| 18 | 78 | 84 | | |
| | 27% | 35% | | |
| 19 | 150 | 480 | | |
| | 64% | 39% | | |
| 20 | 800 | 68 | | |
| | 15% | 67% | | |
| 21 | 1600 | 160 | | |
| | 34% | 34% | | |
| 22 | 160 | 58 | | |
| | 89% | 51% | | |
| 23 | 1200 | 94 | | |
| | 91% | 61% | | |
| 24 | 1300 | 320 | | |
| | 52% | 47% | | |
| 25 | 570 | 170 | | |
| | 65% | 51% | | |
| 26 | 16 | 34 | | |
| | 110% | 61% | | |
| 27 | 100 | 170 | | |
| | 100% | 55% | | |
| 28 | 30 | 65 | | |
| | 100% | 61% | | |
| 29 | 140 | 46 | | |
| | 75% | 36% | | |
| 30 | 330 | 63 | 48 | 21 |
| | 40% | 12% | | |
| 31 | 1000 | 140 | | |
| | 64% | 57% | | |
| 32 | 40 | 29 | | |
| | 110% | 62% | | |
| 33 | 870 | 160 | | |
| | 25% | 30% | | |

[a]Span was measured as a percentage of the maximum [$^3$H]CP55940 signal in CHO cell membrane preparations overexpressing hCB1 or hCB2 receptors.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

That which is claimed is:

1. A compound of Formula (I):

(I)

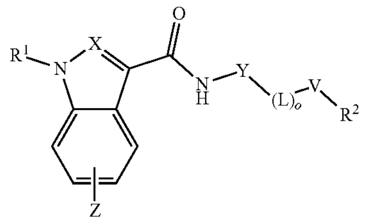

wherein $R^1$ is unsubstituted or substituted $C_{1-10}$ alkyl, $C_{1-10}$ haloalkyl, $(CH_2)_n$-cycloalkyl, $(CH_2)_n$-heterocyclyl, $(CH_2)_n$-aryl, or $(CH_2)_n$-heteroaryl;

n is 1, 2, or 3;

X is CH or N;

Y is $CH(CH_3)$ or $C(CH_3)_2$;

V is divalent aryl, heteroaryl, cycloalkyl, heterocyclyl, $C_{2-3}$ alkyl, or $C_{2-3}$ alkenyl;

Z is H, F, Cl, $CF_3$, Me, CN, OMe, $OCF_3$, or $OCHF_2$;

$R^2$ is (i) $(CH_2)_pC(O)NHR^a$;

(ii) $NHC(O)R^b$;

(iii) $NR^cC(O)NHR^a$; or (iv) $NH(C{=}NR)NHR^a$;

p is 0, 1, or 2;

$R^a$ is H, $C_{1-4}$ alkyl, $C_{3-6}$ cycloalkyl, heterocyclyl, aryl, or heteroaryl;

$R^b$ is $C_{1-4}$ alkyl, $C_{3-6}$ cycloalkyl, heterocyclyl, aryl, or heteroaryl;

$R^c$ is H or $C_{1-4}$ alkyl; and $R^d$ is H, CN, $C_{1-4}$ alkyl, or $C_{3-6}$ cycloalkyl, or a pharmaceutically acceptable salt thereof.

2. The compound of claim 1, wherein X is N.

3. The compound of claim 2, wherein Y is $C(CH_3)_2$.

4. The compound of claim 1, wherein V is divalent aryl, heteroaryl, cycloalkyl, or heterocyclyl.

5. The compound of claim 1, wherein $R^2$ is (i) $(CH_2)_pC(O)NHR^a$;

(ii) $NHC(O)NHR^a$, wherein $R^a$ is H, $C_{1-4}$ alkyl, $C_{3-6}$ cycloalkyl, heterocyclyl, aryl, or heteroaryl.

6. The compound of claim 1, wherein $R^2$ is (i) $(CH_2)_pC(O)NHR^a$; or (ii) $NHC(O)NHR^a$, wherein $R^a$ is H, $C_{1-4}$ alkyl, $C_{3-6}$ cycloalkyl, heterocyclyl, aryl, or heteroaryl.

7. The compound of claim 1, wherein n is 1.

8. The compound of claim 1, wherein Z is H or F.

9. A compound having the structure of any of compounds 10-33 as set forth in Table 1.

10. A pharmaceutical composition comprising a compound of claim 1 and one or more pharmaceutically acceptable carrier.

* * * * *